United States Patent
Yeung et al.

(10) Patent No.: US 9,138,254 B2
(45) Date of Patent: Sep. 22, 2015

(54) TISSUE REPAIR WITH SPACE-SEEKING SPIRALS OF FILAMENT

(75) Inventors: Jeffrey Eric Yeung, San Jose, CA (US); Teresa Tan Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 0 days.

(21) Appl. No.: 13/261,607

(22) PCT Filed: Mar. 23, 2012

(86) PCT No.: PCT/US2012/000158
§ 371 (c)(1),
(2), (4) Date: Mar. 1, 2013

(87) PCT Pub. No.: WO2012/128829
PCT Pub. Date: Sep. 27, 2012

(65) Prior Publication Data
US 2013/0289599 A1 Oct. 31, 2013

Related U.S. Application Data

(60) Provisional application No. 61/465,804, filed on Mar. 23, 2011, provisional application No. 61/518,489, filed on May 7, 2011, provisional application No. 61/572,820, filed on Jul. 21, 2011.

(51) Int. Cl.
*A61B 17/06* (2006.01)
*A61B 17/34* (2006.01)
(Continued)

(52) U.S. Cl.
CPC ......... *A61B 17/3468* (2013.01); *A61B 17/7094* (2013.01); *A61B 17/8852* (2013.01);
(Continued)

(58) Field of Classification Search
CPC ............... A61B 17/06066; A61B 17/0469; A61B 17/06; A61B 17/0482; A61B 17/06004; A61B 2017/00004; A61B 2017/0414
USPC ........................ 606/185, 222–224, 225–231
See application file for complete search history.

(56) References Cited

U.S. PATENT DOCUMENTS 8,226,600 B2 7/2012 Yeung
8,361,007 B2 1/2013 Yeung
(Continued)

OTHER PUBLICATIONS

Stairmand JW, Holm S, Urban JPG: Factor influencing oxygen concentration gradients in disc, Spine, vol. 16, 4, 444-449, 1991.
(Continued)

*Primary Examiner* — Mary Hoffman
*Assistant Examiner* — Tara R Carter
(74) *Attorney, Agent, or Firm* — Carol Titus; GSS Law Group

(57) ABSTRACT

A distal portion of a filament is extended beyond the distal end of a needle with a gripper. The needle with the extended filament is inserted into a cannula with snagging points at the distal opening of the cannula in tissue. The snagging points of the cannula hook and retain the distal portion of the filament. During partial withdrawal of the needle, a section of filament is deposited in the lumen of the cannula between the distal ends of the needle and cannula. When the needle is re-advanced, the section of filament is expelled or pushed out of the cannula into tissue. The needle is then rotated; the gripper engages and spirals the expelled filament, burrowing into tissue. The needle can further advanced to push and pack the spiral of filament deep into the tissue. The knot-like filament spiral is individually formed by rotation of the needle and friction between the extended filament and tissue. The process of needle partial withdrawal, re-advancement, rotation and pushing is repeated to pack and fill the tissue with interconnecting spirals of filament to prevent migration from tissue. Spiraling of the filament driven by the rotating needle is space seeking, filling, fitting or conforming to fortify, bulk, fill, cushion or repair the tissue. Bulking with filament spirals can repair degenerated disc, urinary incontinence, fecal incontinence or other defective tissue. The filament spirals can also be used as a suture anchor deep within tissue.

34 Claims, 26 Drawing Sheets

(51) Int. Cl.
| | |
|---|---|
| *A61B 17/88* | (2006.01) |
| *A61F 2/44* | (2006.01) |
| *A61F 2/46* | (2006.01) |
| *A61B 17/70* | (2006.01) |
| *A61B 17/00* | (2006.01) |
| *A61F 2/30* | (2006.01) |
| *A61B 17/04* | (2006.01) |

(52) U.S. Cl.
CPC .............. *A61F2/442* (2013.01); *A61F 2/4611* (2013.01); *A61B 17/0483* (2013.01); *A61B 17/7061* (2013.01); *A61B 2017/00867* (2013.01); *A61F 2002/30289* (2013.01); *A61F 2002/30294* (2013.01); *A61F 2002/30677* (2013.01); *A61F 2002/4495* (2013.01); *A61F 2002/4635* (2013.01); *A61F 2310/0061* (2013.01); *A61F 2310/0097* (2013.01); *A61F 2310/00598* (2013.01); *A61F 2310/00976* (2013.01); *A61F 2310/00982* (2013.01)

(56) References Cited

U.S. PATENT DOCUMENTS

| | | | |
|---|---|---|---|
| 8,449,490 | B2 | 5/2013 | Yeung |
| 2010/0030241 | A1* | 2/2010 | Yeung et al. .................. 606/146 |

OTHER PUBLICATIONS

Maroudas A, Stockwell RA, Nachemson A, Urban J: Factors involved in the nutrition of the human lumbar intervertebral disc, J. Anat., 120, 113-130, 1975.
Diamant B, Karlsson J, Nachemson A: Correlation between lactate levels and pH of patients with lumbar rizopathies, Experientia, 24, 1195-6, 1968.
Nachemson A: Intradiscal measurements of pH in patients with lumbar rhizopathies. Acta Orthop Scand, 40, 23-43, 1969.
Keshari KR, Lotz JC, Link TM, Hu S, Majumdar S, Kurhanewicz J: Lactic acid and proteoglycans as metabolic markers for discogenic back pain, Spine, vol. 33(3):312-317, 2008.
Urban JP, Smith S, Fairbank JCT: Nutrition of the Intervertebral Disc, Spine, 29 (23), 2700-2709, 2004.
Benneker LM, Heini PF, Alini M, Anderson SE, Ito K: Vertebral endplate marrow contact channel occlusions & intervertebral disc degeneration, Spine V30, 167-173, 2005.
Holm S, Maroudas A, Urban JP, Selstam G, Nachemson A: Nutrition of the intervertebral disc: solute transport and metabolism, Connect Tissue Res., 8(2): 101-119, 1981.
Kitano T, Zerwekh J, Usui Y: Biochemical changes associated with the symptomatic human intervertebral disk, Clinical Orthopaedics and Related Research, 293, 372-377, 1993.
Scott JE, Bosworth TR, Cribb AM, Taylor JR: The chemical morphology of age-related changes in human intervertebral disc glycosaminoglycans, J. Anat., 184, 73-82, 1994.
Diamant B, Karlsson J, Nachemson A: Correlation between lactate levels and pH of patients with lumbar rizopathies, Experientia, 24, 1195-1196, 1968.
Nachemson A: Intradiscal measurements of pH in patients with lumbar rhizopathies, Acta Orthop Scand, 40, 23-43, 1969.
Dunlop RB, Adams MA, Hutton WC: Disc space narrowing and the lumbar facet joints, Journal of Bone and Joint Surgery—British Volume, vol. 66-B, Issue 5, 706-710, 1984.
Andersson GBJ, Schultz AB: Effects of fluid on mechanical properties of intervertebral discs, J. Biomechanics, vol. 12, 453-458, 1979.
Gruber H.E., Leslie K., Ingram J.: Colony formation and matrix production by human anulus cells: modulation in three-dimensional culture, Spine, Jul. 1, 29(13), E267-274, 2004.
Johnstone B, Bayliss MT: The large proteoglycans of the human intervertebral disc, Changes in their biosynthesis and structure with age, Spine, Mar. 15;20(6):674-84, 1995.
Ohshima H, Urban JP: The effect of lactate and pH on proteoglycan and protein synthesis rates in the intervertebral disc. Spine, Sep:17(9), 1079-82, 1992.

* cited by examiner

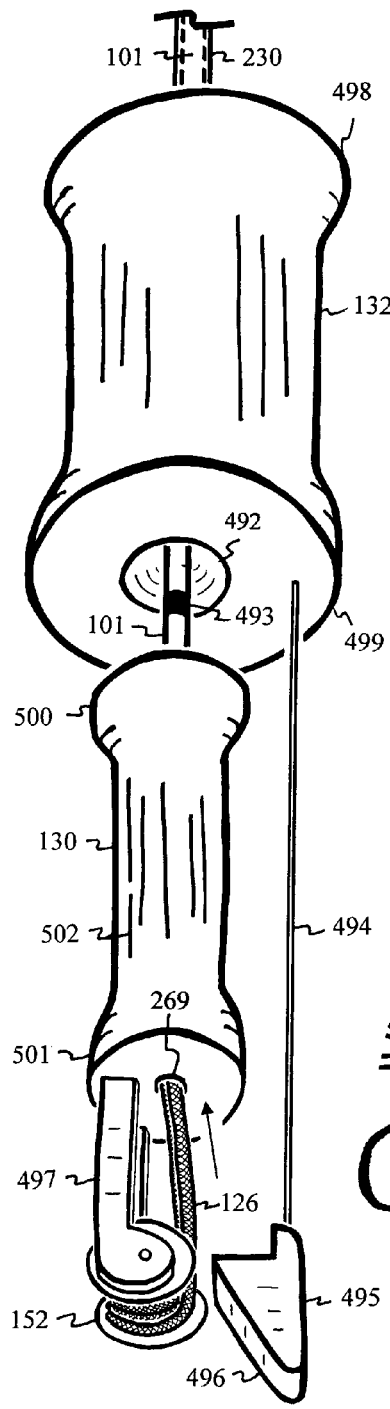
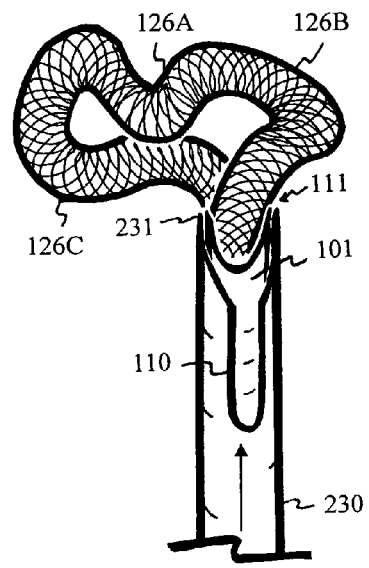
Figure 26
Figure 27
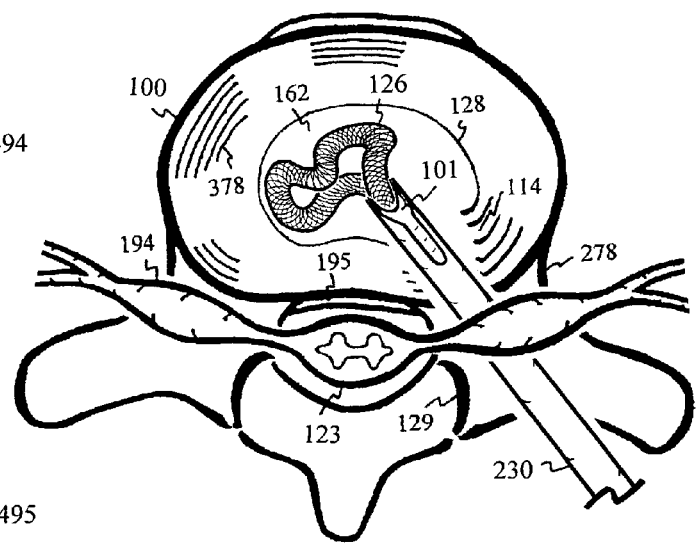
Figure 28

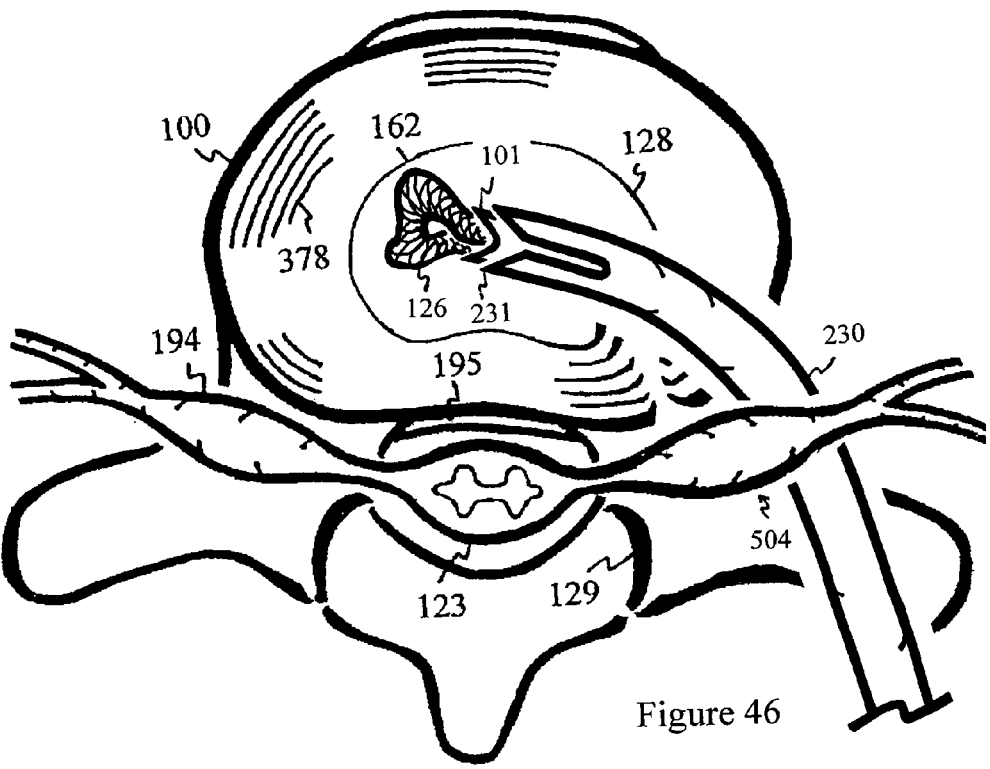
Figure 46
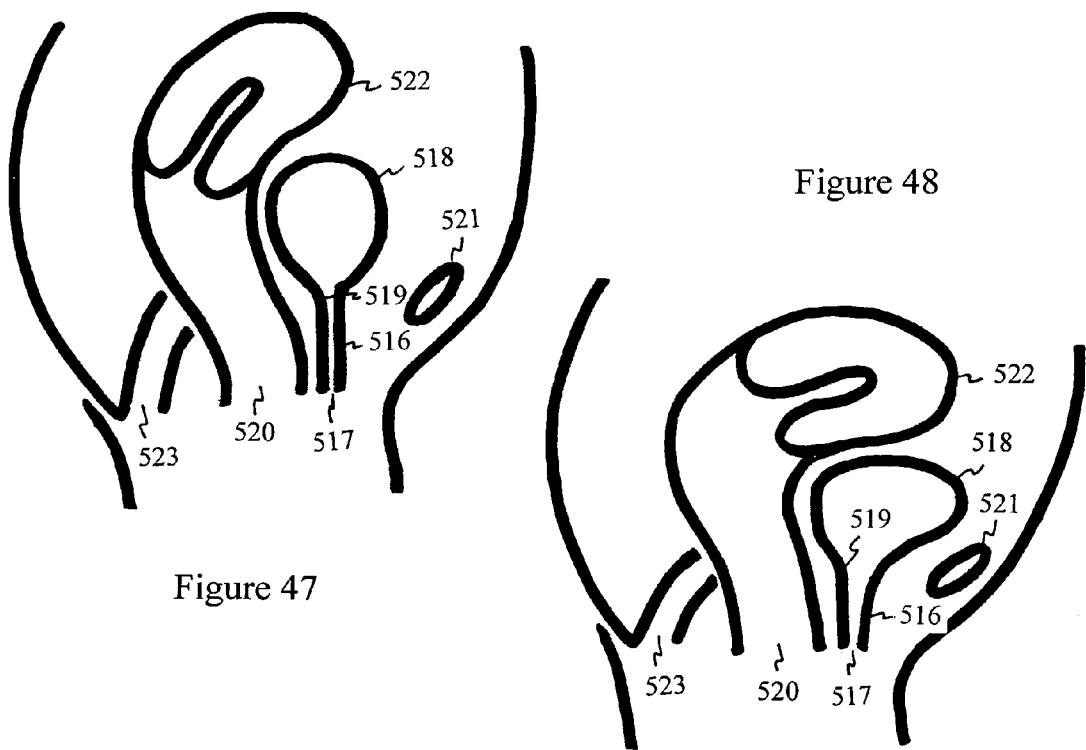
Figure 47
Figure 48

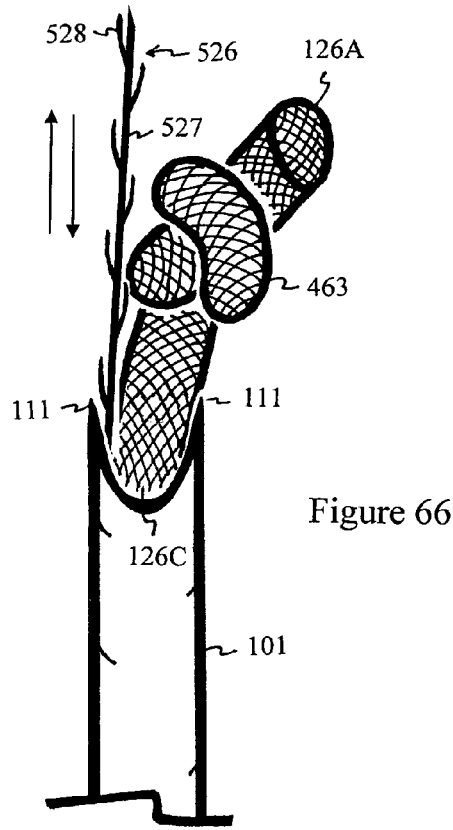
Figure 66
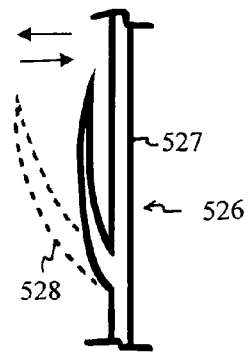
Figure 67
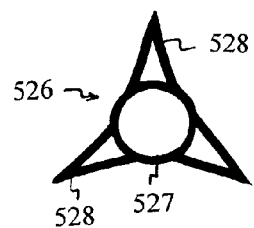
Figure 68
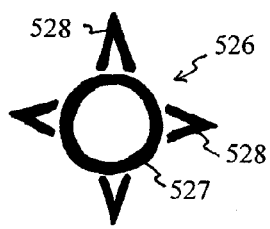
Figure 69
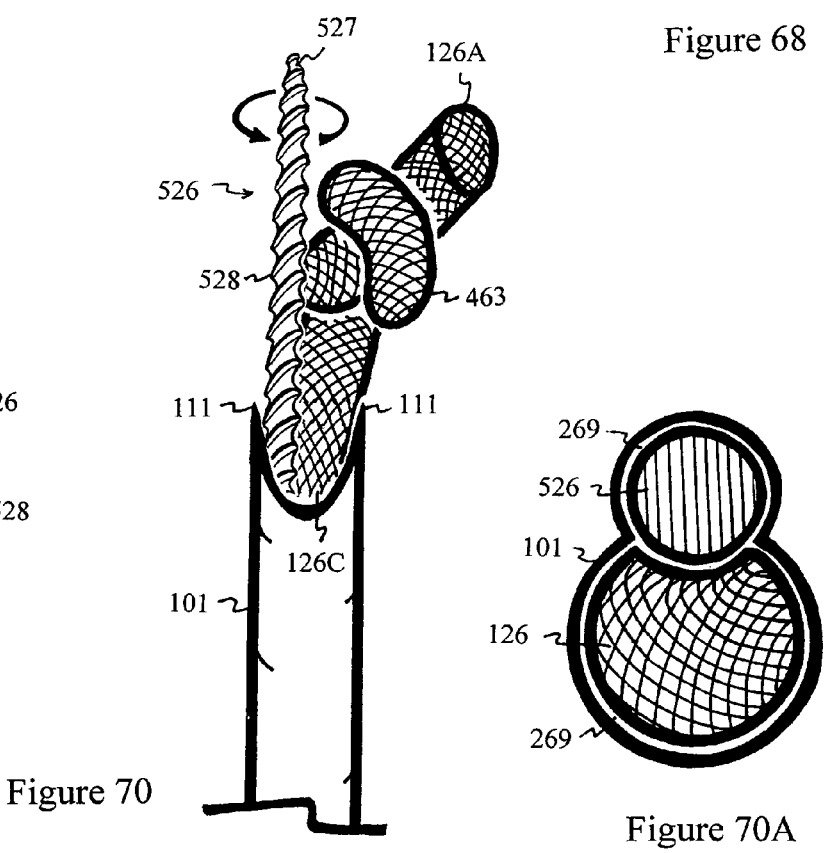
Figure 70
Figure 70A

TISSUE REPAIR WITH SPACE-SEEKING SPIRALS OF FILAMENT

CROSS-REFERENCES TO OTHER APPLICATIONS

This application is the national phase of PCT/US2012/000,158, filed on Mar. 23, 2012. This application has priority of U.S. Provisional Applications: 61/465,804 filed on Mar. 23, 2011, 61/518,489 filed on May 7, 2011, and 61/572,820 filed on Jul. 21, 2011.

FIELD OF INVENTION

This invention relates to a spiraling device using filament to fill, pack and repair tissue, including intervertebral disc, urethral and fecal sphincters.

BACKGROUND

Chronic back pain is an epidemic. Nerve impingement is not seen by CT or MRI in about 85% of back pain patients [Deyo R A, Weinstein J N: Low back pain, N Eng J Med, 344(5) February, 363-370, 2001. Boswell M V, et. al.: Interventional Techniques: Evidence-based practice guidelines in the management of chronic spinal pain, Pain Physician, 10:7-111, ISSN 1533-3159, 2007]. In fact, lumbar disc prolapse, protrusion, or extrusion account for less than 5% of all low back problems, but are the most common causes of nerve root pain and surgical interventions (Manchikanti L, Derby R, Benyamin R M, Helm S, Hirsch J A: A systematic review of mechanical lumbar disc decompression with nucleoplasty, Pain Physician; 12:561-572 ISSN 1533-3159, 2009). The cause of chronic back pain in most patients has been puzzling to both physicians and patients.

Studies indicate back pain is correlated with high lactic acid in the disc. Leakage of the acid causes acid burn and persistent back pain. In addition, as the disc degenerates and flattens, the compressive load is shifted from the flattened disc to facet joints, causing strain and pain. Both lactic acid burn and strain of the facet joints are not visible under CT or MRI.

Urinary incontinence is common among women after multiple pregnancies. Weight of the fetus partially rests on the bladder, flattening and widening the bladder neck and urethral lumen. The sphincteric action of the urethral smooth muscle cannot contract far enough to close the widened lumen for coaptation of urethral mucosa, resulting in urinary incontinence.

SUMMARY OF INVENTION

A distal portion of a filament is extended beyond a distal end of a needle with a gripper. The needle with the extended filament is inserted into a cannula with snagging points at the distal opening of the cannula. The snagging points of the cannula hook and retain the distal portion of the filament. During partial withdrawal of the needle, a section of filament is deposited in the lumen of the cannula between the distal ends of the needle and cannula. When the needle is re-advanced, the section of filament is expelled or pushed out of the cannula into tissue. The needle is then rotated; the gripper engages and spirals the expelled filament to burrow into tissue. The needle can be further advanced to push and pack the spiral of filament deep into the tissue. The process of needle partial withdrawal, re-advancement, rotation and pushing is repeated to pack and fill the tissue with interconnecting spirals of filament. Spirals of filament repair intervertebral discs to relieve back pain, or bulk sphincters to treat urinary or fecal incontinence.

REFERENCE NUMBERS

100 Intervertebral disc
100A L5-S1 disc
100B L4-5 disc
100C L3-4 disc
101 Needle
102 Spinal needle
103 Guide wire or tube
104 Strand in filament
105 Endplate
106A Superior diffusion zone
106B Inferior diffusion zone
107 Capillaries
108 Calcified layers
109 Vascular buds in endplates
110 Window of cannula
111 Filament gripper of filament needle
112 Extension bar
113 Indentation between snagging points
114 Annular delamination
115 Epiphysis
116 Lumen of dilator
118 Sensory nerve
119 Epidural space
120 Indentation between grippers
121 Fissure
123 Spinal cord
124 Pores of sponge filament
126 Filament, shunt or disc shunt
126A U-section or distal portion of filament
126B Second proximal portion of filament
126C First proximal portion of filament
127 Cover or wrapper of filament
128 Nucleus pulposus
129 Facet joint
130 Filament needle handle
131 Nutrients, oxygen and pH buffering
132 Cannula handle
133 Transverse process
134 Spinous process
135 Lamina
140 Ilium or iliac crest
142 Superior articular process
143 Inferior articular process
152 Bobbin
159 Vertebral body
160 Biosynthetic product or molecule
162 Lactic acid
163 Contrast agent
184 Hole or void in tissue
193 Muscle
194 Spinal nerve root
195 Posterior longitudinal ligament
220 Dilator
230 Cannula
231 Snagging point, distal edge or rim of cannula
268 Lumen of cannula
269 Lumen of filament needle
276 Syringe
277 Cell
278 Pedicle
378 Annulus or annular layer 460 Thin spinal needle
462 Anchor or toggle
463 Knot
492 Funnel into lumen of cannula
493 Marker on filament needle
494 Flexible holder of the latch
495 Latch
496 Slope or slanted surface of latch
497 Holder of bobbin
498 Distal protrusion of cannula handle
499 Proximal protrusion of cannula handle
500 Distal protrusion of filament needle handle
501 Proximal protrusion of filament needle handle
502 Friction ridges of needle handle
504 Kambin's Triangle (safe entry into disc)
505 Skin
516 Urethra
517 Urethral lumen
518 Bladder
519 Bladder neck
520 Vagina
521 Pubis
522 Uterus
523 Rectum
524 Posterior wall of urethra
525 Forceps
526 Filament advancer
527 Stem of filament advancer
528 Barbs or thread of filament advancer
529 Cone head of dilator
530 Removable luer lock or dilator handle
531 Luer lock for syringe
532 Urethral smooth muscle
533 Urethral lumen mucosa

DESCRIPTION OF THE DRAWINGS

FIG. 26 shows handle 132 of cannula, handle 130 of filament needle and a spool of filament 126 on a bobbin 152 for feeding into the lumen 269 during withdrawal of the needle 101.

FIG. 27 shows re-advancement of the filament needle 101 from FIG. 25, pushing the deposited filament 126B, 126C out of the cannula 230.

FIG. 28 shows filament 126 in nucleus 128 by re-advancing the needle 101.

FIG. 46 shows an elastically curved cannula 230 directing a flexible filament needle 101 into the center of the disc 100.

FIG. 47 shows normal position of a bladder neck 519 of a woman with urinary control.

FIG. 48 shows funneling or widening of a bladder neck 519 leading to urinary incontinence.

FIG. 66 shows a filament advancer 526 with resiliently collapsible barbs 528, moving in cyclical distal-proximal motion to advance or propel the filament 126 out of the needle 101.

FIG. 67 shows open and closed positions of the resiliently collapsible barb 528.

FIG. 68 shows an axial or vertical view of the filament advancer 526 with resiliently collapsible barbs 528 approximately 120 degrees apart.

FIG. 69 shows an axial or vertical view of the filament advancer 526 with resiliently collapsible barbs 528 approximately 90 degrees apart.

FIG. 70 shows a rotational auger 526 as a filament advancer 526 to convey or propel the filament 126 out the needle 101.

FIG. 70A shows a cross section of a needle 101 with a lumen 269 configuration to accommodate the filament advancer 526 and filament 126.

DETAILED DESCRIPTION OF THE EMBODIMENTS

Figure 1:
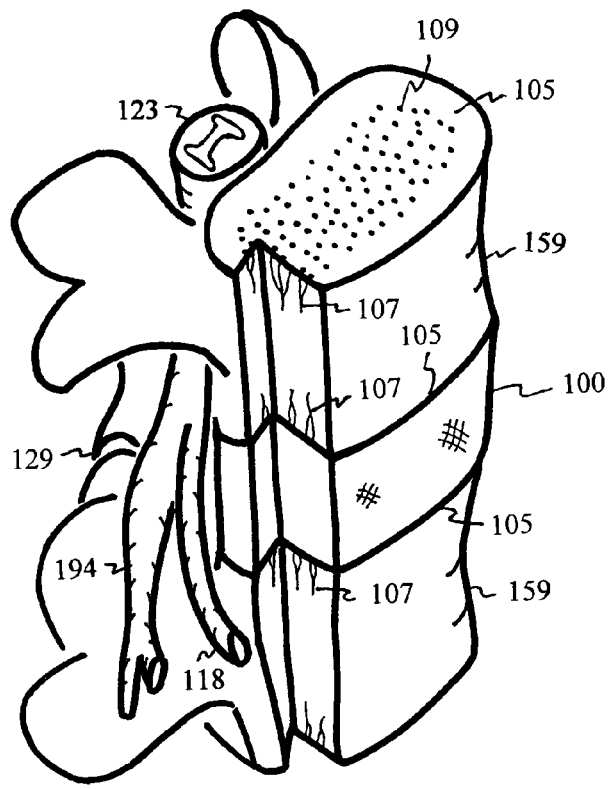
FIG. 1 shows capillaries 107 in vertebral bodies 159 providing oxygen, nutrients and pH buffer for the avascular intervertebral disc 100 through diffusion.
Figure 2:
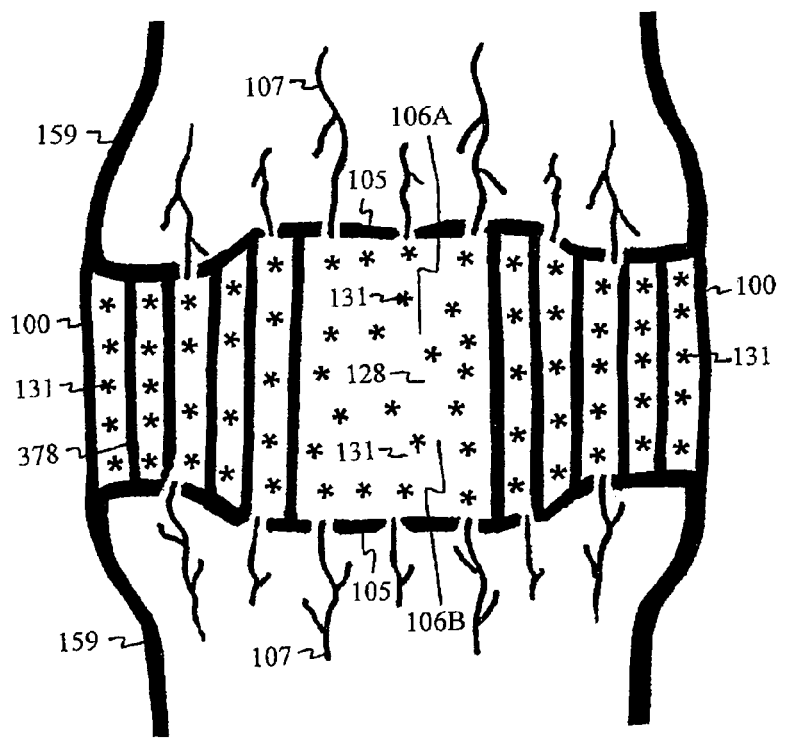
FIG. 2 shows a longitudinal view of a healthy spinal segment with nutrients 131 supplied by capillaries 107 at the vertebral bodies 159 and endplates 105 to feed the cells within the disc 100.

Intervertebral discs are avascular (no blood vessels). Nutrients, oxygen and pH buffer 131 essential for disc cells are supplied by the capillaries 107 in the vertebral bodies 159 and diffused from superior and inferior endplates 105 into the disc 100, as shown in FIGS. 1 and 2. Blood pH is tightly regulated between 7.35 and 7.45, mainly by the pH buffering bicarbonate dissolved in blood plasma diffused through superior and inferior endplates 105 into the disc 100.

Figure 3:
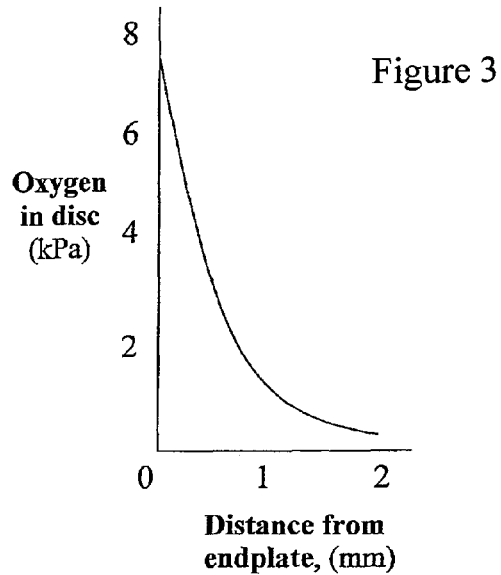
FIG. 3 shows a graph of distance into disc from endplate versus oxygen concentration.

However, depth of diffusion is shallow into thick human discs 100. Depth of oxygen diffusion from the endplates 105 is summarized in FIG. 3 (Stairmand J W, Holm S, Urban J P G: Factor influencing oxygen concentration gradients in disc, Spine, Vol. 16, 4, 444-449, 1991). Similarly, depths of glucose diffusion are less than 3 mm from superior and inferior endplates (Maroudas A, Stockwell R A, Nachemson A, Urban J: Factors involved in the nutrition of the human lumbar intervertebral disc: Cellularity and diffusion of glucose in vitro, J. Anat., 120, 113-130, 1975). Nearly all animals have thin discs; depths of diffusion of oxygen and nutrients seem to be sufficient. Lumbar discs of a large sheep weighing 91 kg (200 pounds) are less than 3 mm thick. However, human lumbar discs are about 7-12 mm thick. Mid layers of our thick discs 100 suffer severe oxygen and nutritional deficiency.

Figure 4:
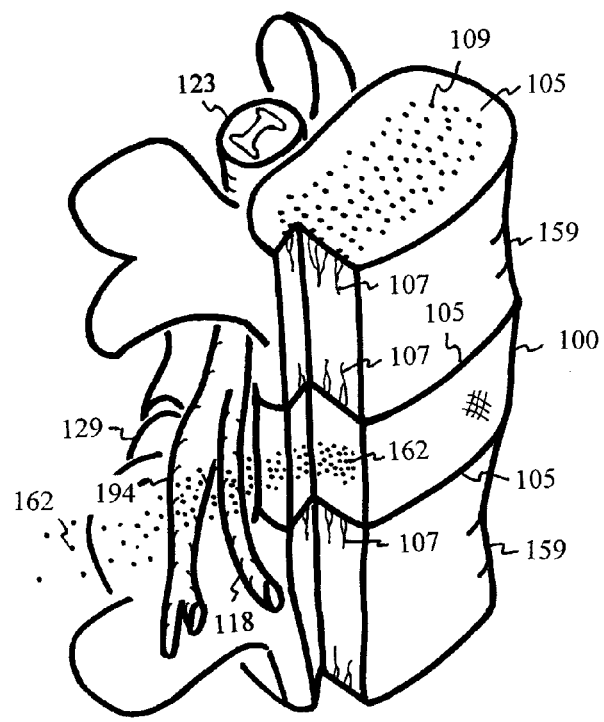
FIG. 4 shows anaerobic production of lactic acid 162 in the mid layer of the disc 100, leaking and burning sensory nerve 118 and spinal nerve 194.
Figure 5:
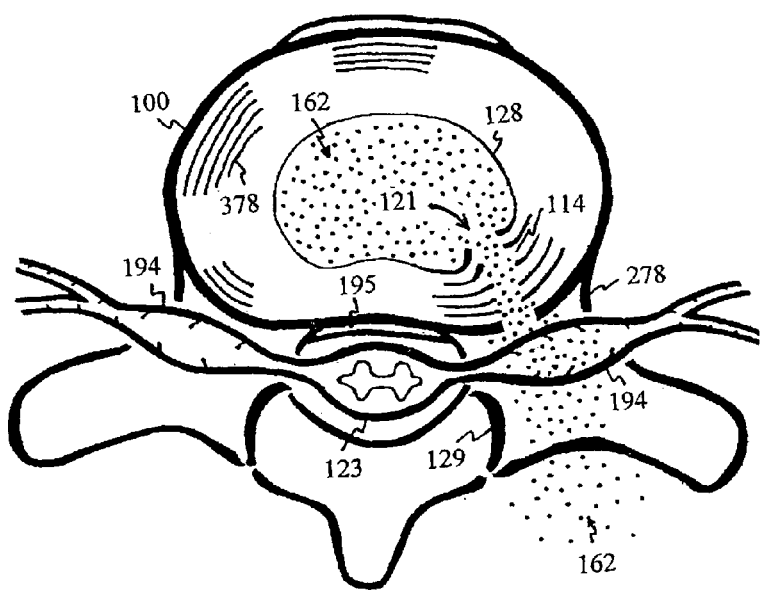
FIG. 5 shows leakage of lactic acid 162, burning or irritating the spinal nerve 194.
Figure 6:
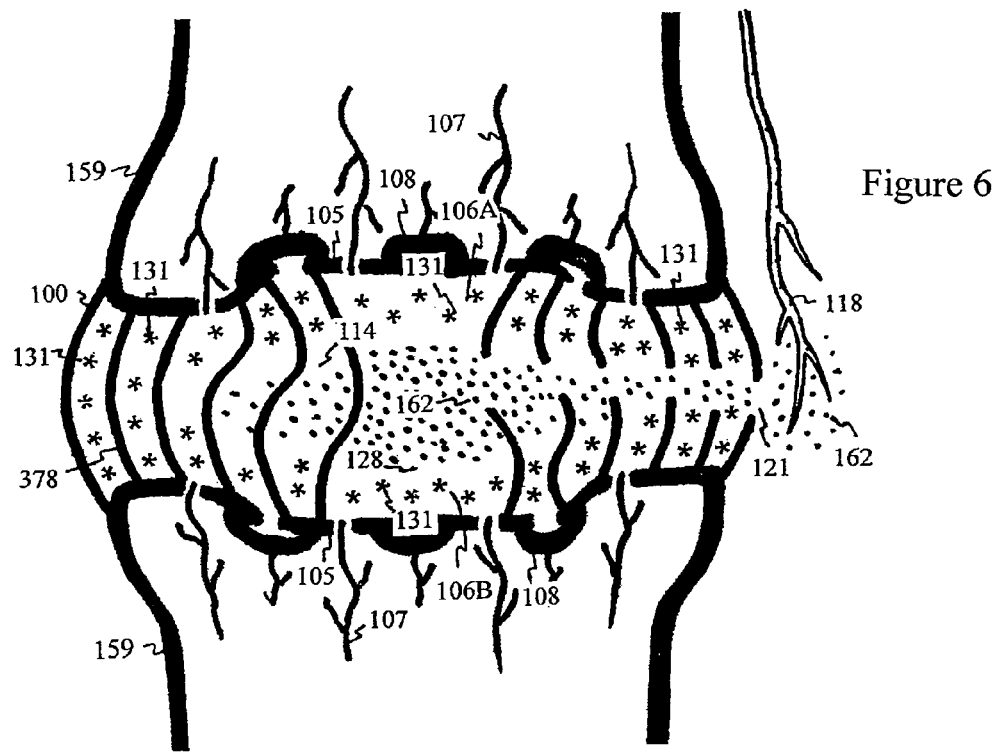
FIG. 6 shows calcified layers 108 at the endplates 105, blocking diffusion of nutrient, oxygen and pH buffer 131 from capillaries 107, forming and leaking lactic acid 162 to nerve 118.

Under anaerobic condition within the mid layer, lactic acid 162 is produced and leaked from the nucleus 128 through fissures 121 to burn surrounding nerves 118, 194 causing persistent back pain, as depicted in FIGS. 4-6. Some patients experience leg pain without visible nerve impingement under MRI or CT. Lactic acid 162 can leak from the nucleus 128 through fissures 121 to spinal nerves 194, causing leg pain as depicted in FIGS. 4-5. Leg pain without visible impingement is commonly called chemical radiculitis.

High lactic acid content in discs correlates with back pain. In fact, dense fibrous scars and adhesions, presumably from lactic acid 162 burn, can be found around nerve roots 194 during spinal surgery [Diamant B, Karlsson J, Nachemson A: Correlation between lactate levels and pH of patients with lumbar rizopathies, Experientia, 24, 1195-6, 1968. Nachemson A: Intradiscal measurements of pH in patients with lumbar rhizopathies. Acta Orthop Scand, 40, 23-43, 1969. Keshari K R, Lotz J C, Link T M, Hu S, Majumdar S, Kurhanewicz J: Lactic acid and proteoglycans as metabolic markers for discogenic back pain, Spine, Vol. 33(3):312-317, 2008].

Figure 7:
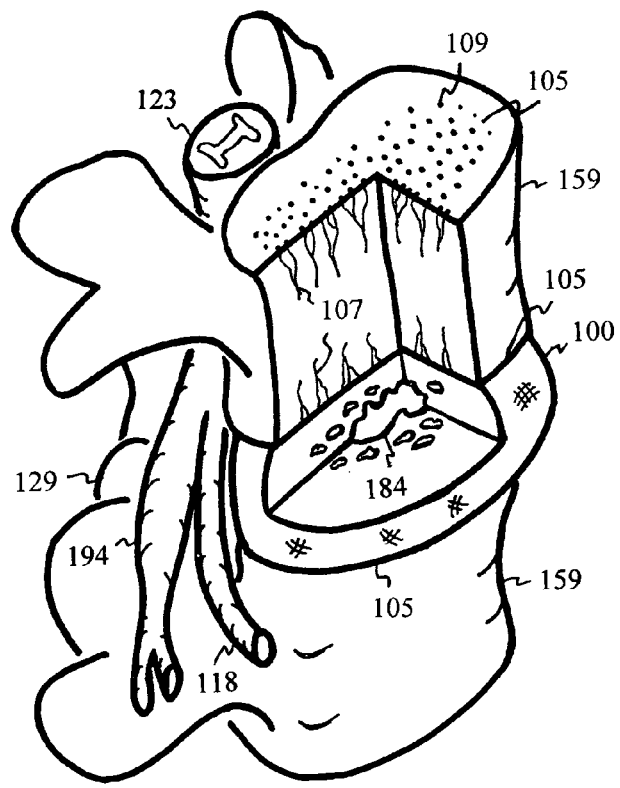
FIG. 7 shows vacuoles 184 in the disc 100 from degradation of proteoglycans to release sugars for maintaining survival of disc cells.

As we age, calcified layers 108 form and accumulate at the endplates 105, blocking capillaries 107 and further limiting the depth of diffusion of nutrients/oxygen/pH buffer 131 into the disc 100, as shown in FIG. 6. Mid layers of the disc 100 suffer chronic and severe starvation and anaerobic conditions. Disc cells can survive without oxygen, but die without sugars. Nucleus 128 contains glycosaminoglycans with covalently bonded sugars, essential for retaining water in the disc 100. Degradation of glycosaminoglycans to release sugars for consumption allows disc cells to survive, but initiates compositional and structural change, creating voids 184 and loosely packed nucleus matrix in a degenerated disc 100, as shown in FIG. 7, [Urban J P, Smith S, Fairbank J C T: Nutrition of the Intervertebral Disc, Spine, 29 (23), 2700-2709, 2004. Benneker L M, Heini P F, Alini M, Anderson S E, Ito K: Vertebral endplate marrow contact channel occlusions & intervertebral disc degeneration, Spine V30, 167-173, 2005. Holm S, Maroudas A, Urban J P, Selstam G, Nachemson A: Nutrition of the intervertebral disc: solute transport and metabolism, Connect Tissue Res., 8(2): 101-119, 1981].

| Composition Change of the Intervertebral Discs (approximation) | | | |
|---|---|---|---|
| | Normal Discs | Painful Discs | % Change from Normal Discs |
| Glycosaminoglycans | 27.4 ± 2.4% | 14.1 ± 1.1% | −48.5% |
| Collagen | 22.6 ± 1.9% | 34.8 ± 1.4% | +54% |
| Water content | 81.1 ± 0.9% | 74.5 ± 1% | −8.1% |
| Acidity | pH 7.14 [$H^+$]: 7.20 × $10^{-8}$ | pH 6.65-5.70 [$H^+$]: 2.23 × $10^{-7}$ to 2.00 × $10^{-6}$ | [$H^+$]: +208% to +2,661% |

(Reference: Kitano T, Zerwekh J, Usui Y, Edwards M, Flicker P, Mooney V: Biochemical changes associated with the symptomatic human intervertebral disk, Clinical Orthopaedics and Related Research, 293, 372-377, 1993. Scott J E, Bosworth T R, Cribb A M, Taylor J R: The chemical morphology of age-related changes in human intervertebral disc glycosaminoglycans from cervical, thoracic and lumbar nucleus pulposus and annulus fibrosus. J. Anat., 184, 73-82, 1994. Diamant B, Karlsson J, Nachemson A: Correlation between lactate levels and pH of patients with lumbar rizopathies, Experientia, 24, 1195-1196, 1968. Nachemson A: Intradiscal measurements of pH in patients with lumbar rhizopathies, Acta Orthop Scand, 40, 23-43, 1969.)

Figure 8:
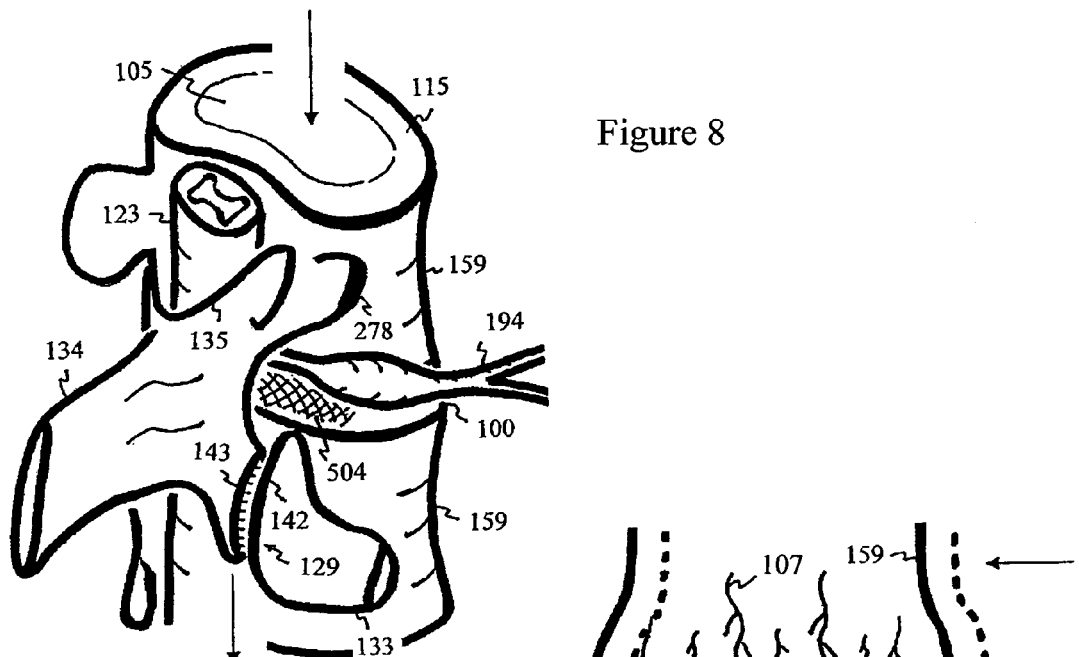
FIG. 8 shows load transfer from the flattened disc 100 to facet joint 129 causing pain.

When glycosaminoglycans diminish, water content and swelling pressure in the nucleus pulposus 128 decrease. The nucleus 128 with reduced swelling pressure can no longer distribute forces evenly against the circumference of the inner annulus 378 to keep the annulus bulging outward. As a result, the inner annulus 378 sags inward while the outer annulus 378 bulges outward, creating annular delamination 114 and weakened annular layers 378, possibly initiating fissure 121 formation depicted in FIGS. 5-6. Holes or vacuoles 184 can be found during dissection of cadaveric discs 100, as shown in FIG. 7. Nucleus pulposi 128 of degenerated discs 100 are usually desiccated, with reduced swelling pressure and decreased capability to sustain compressive loads. The compressive load is thus transferred to the facet joints 129, pressing the inferior articular process 143 against the superior articular process 142 of the facet joint 129, causing strain, wear and/or pain as shown in FIG. 8 (Dunlop R B, Adams M A, Hutton W C: Disc space narrowing and the lumbar facet joints, Journal of Bone and Joint Surgery—British Volume, Vol. 66-B, Issue 5, 706-710, 1984).

Figure 9:
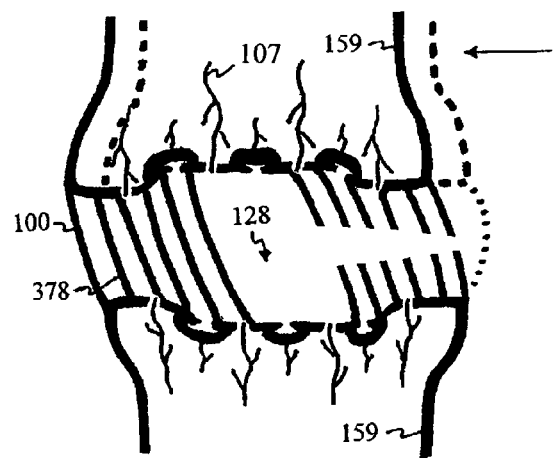
FIG. 9 depicts swaying of a vertebral body 159 above a disc 100 with low-swelling pressure.
Figure 10:
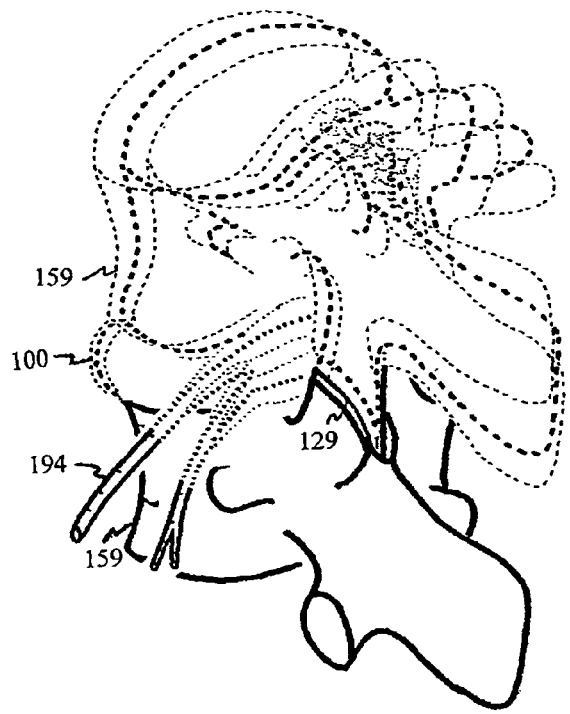
FIG. 10 depicts spinal instability from the low-pressure disc 100, straining and wearing down the facet joints 129.

A disc 100 with reduced swelling pressure is similar to a flat tire with flexible or flabby side walls. The vertebral body 159 above the soft or flabby disc 100 easily shifts or sways, as shown in FIG. 9. This is commonly called segmental or spinal instability. As shown in FIG. 10, the frequent or excessive movement of the vertebral body 159 strains the facet joints 129, which are responsible for limiting the range of segmental mobility. Patients with spinal instability often use their muscles to guard or support their spines to ease facet pain. As a result, muscle tension and aches arise, but are successfully treated with muscle relaxants. Spinal motions, including compression, torsion, extension, flexion and lateral bending, were measured before and after saline injection into cadaveric discs. Intradiscal saline injections into slow leaking cadaveric discs reduced all spinal motions (Andersson G B J, Schultz A B: Effects of fluid on mechanical properties of intervertebral discs, J. Biomechanics, Vol. 12, 453-458, 1979).

Figure 11:
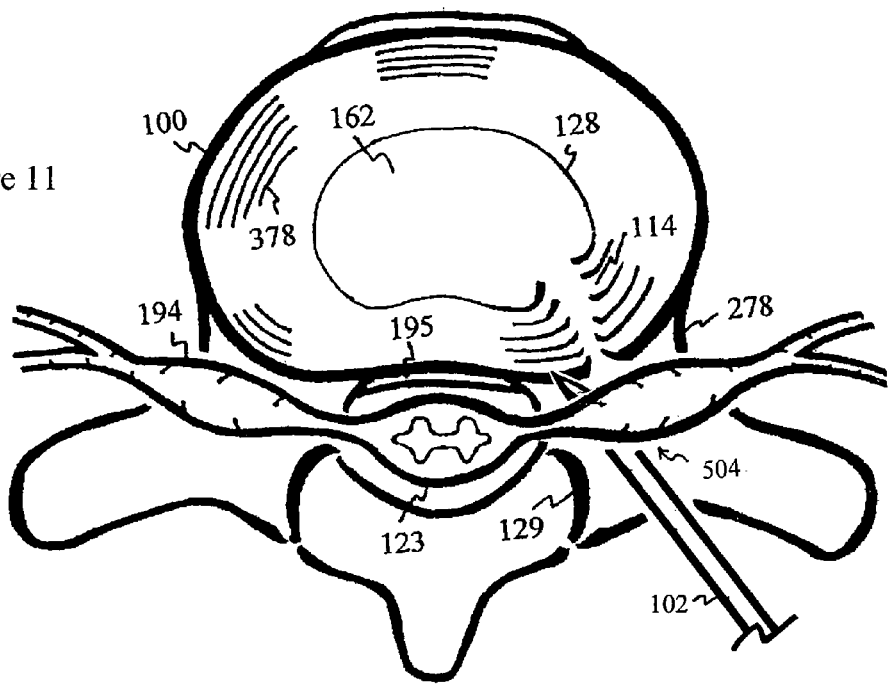
FIG. 11 shows insertion of a spinal needle 102 toward the surface of the degenerated disc 100 to prepare for diagnostic discography.
Figure 12:
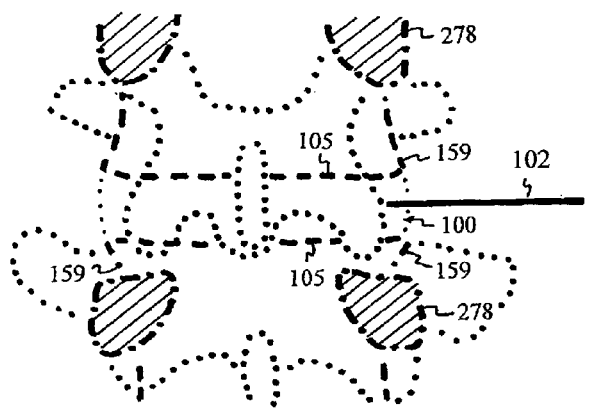
FIG. 12 shows a fluoroscopic anterior-posterior view of the needle 102, about half way past pedicles 278, entering into the disc 100.
Figure 13:
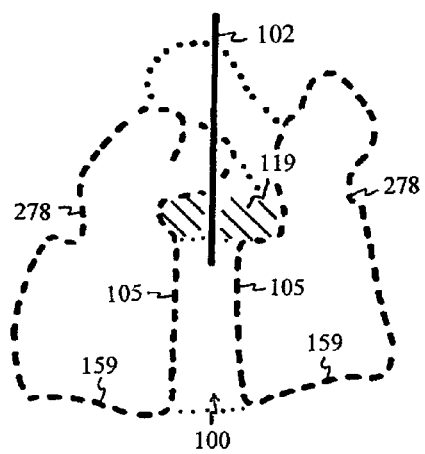
FIG. 13 shows a fluoroscopic lateral view of the needle 102 entering into the disc 100 space, but not into the epidural space 119.

Discography is a common diagnostic technique for identifying or confirming a painful disc 100 before surgical intervention. A spinal needle 102 is guided by a fluoroscope toward the Kambin's Triangle 504 in FIGS. 8 and 11, a posterior-lateral area through which spinal needle 102 can access a lumbar disc 100 safely. The anterior-posterior view in FIG. 12 guides the needle 102 between endplates 105, but does not show the ventral-dorsal location of the needle 102 tip. Before passing the pedicle 278 midway, a lateral fluoroscopic view depicted in FIG. 13 must be taken to ensure the needle 102 is not too dorsal, entering into the epidural space 119. FIG. 13 depicts the lateral fluoroscopic view, showing the needle 101 tip is ventral to the epidural space 119 and can safely enter into the mid layer of the disc 100.

Figure 14:
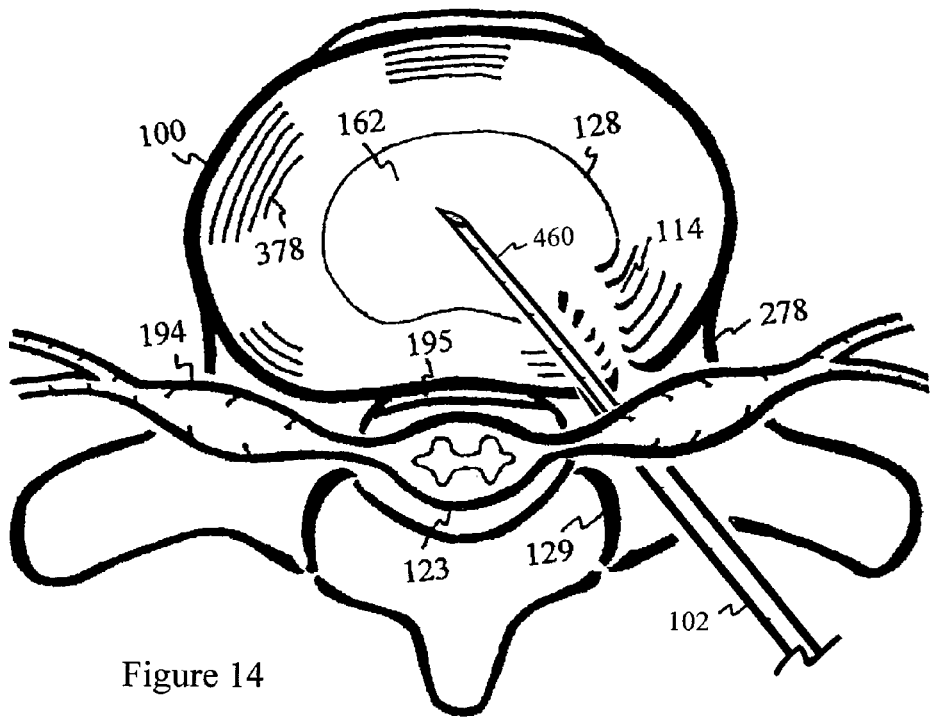
FIG. 14 shows a small spinal needle 460 housed within the spinal needle 102, puncturing into the nucleus pulposus 128 of the degenerated disc 100.
Figure 15:
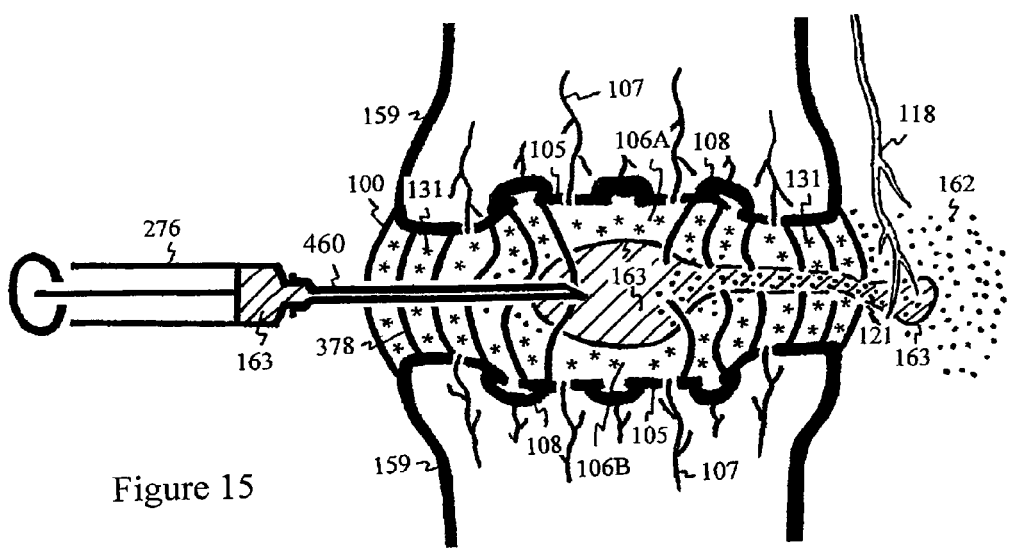
FIG. 15 depicts pain diagnostic discography by flushing lactic acid 162 from disc 100 to sensory nerve 118 with contrast agent 163 to provoke and confirm the excruciating pain.

In literature, sizable disc 100 puncturing or laceration accelerates disc degeneration. In non-painful discs 100, a small spinal needle 460 within the spinal needle 102 is used to puncture the disc 100 as shown in FIG. 14. FIG. 15 shows intradiscal injection of X-ray contrast 163, flushing out lactic acid 162 in the disc 100 through fissures 121 to burn the sensory nerve 118, instantaneously causing excruciating pain and confirming specific painful disc 100. For normal or non-painful discs, discography is nearly painless. The spinal needle 102 is not shown in FIG. 15. The spinal needle 102 in FIGS. 11-16 allows joining of diagnostic discography with therapeutic intervention to relieve back pain during the same visit to save time and reduce pain.

Figure 16:
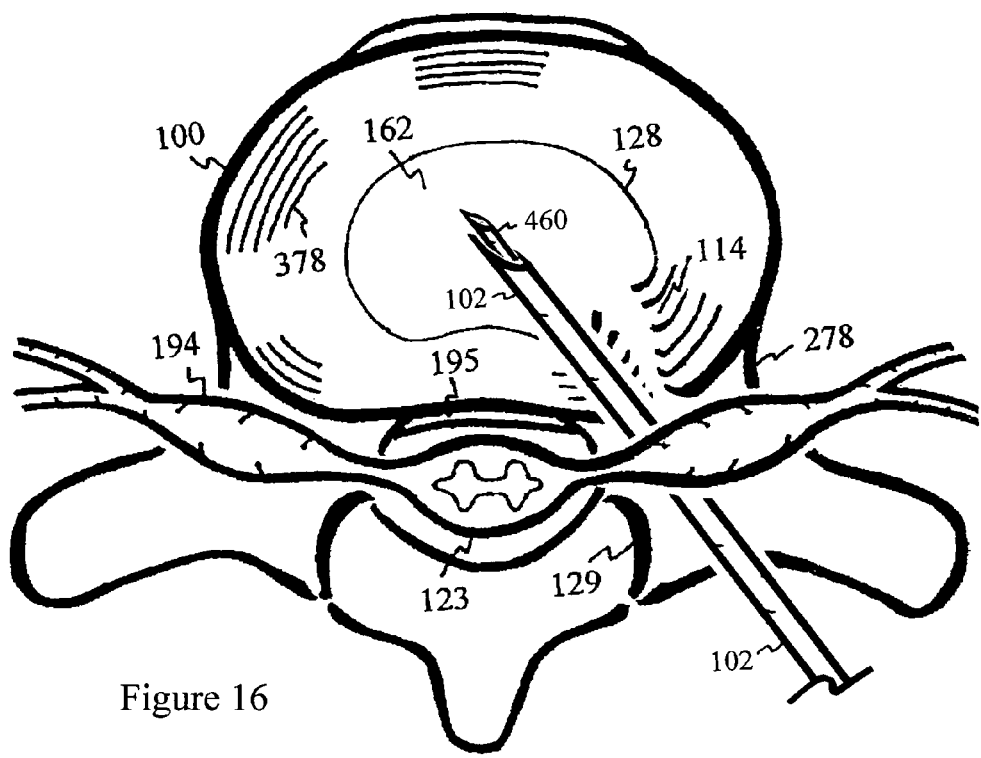
FIG. 16 shows sliding of spinal needle 102 over small spinal needle 460 into nucleus 128.
Figure 18:
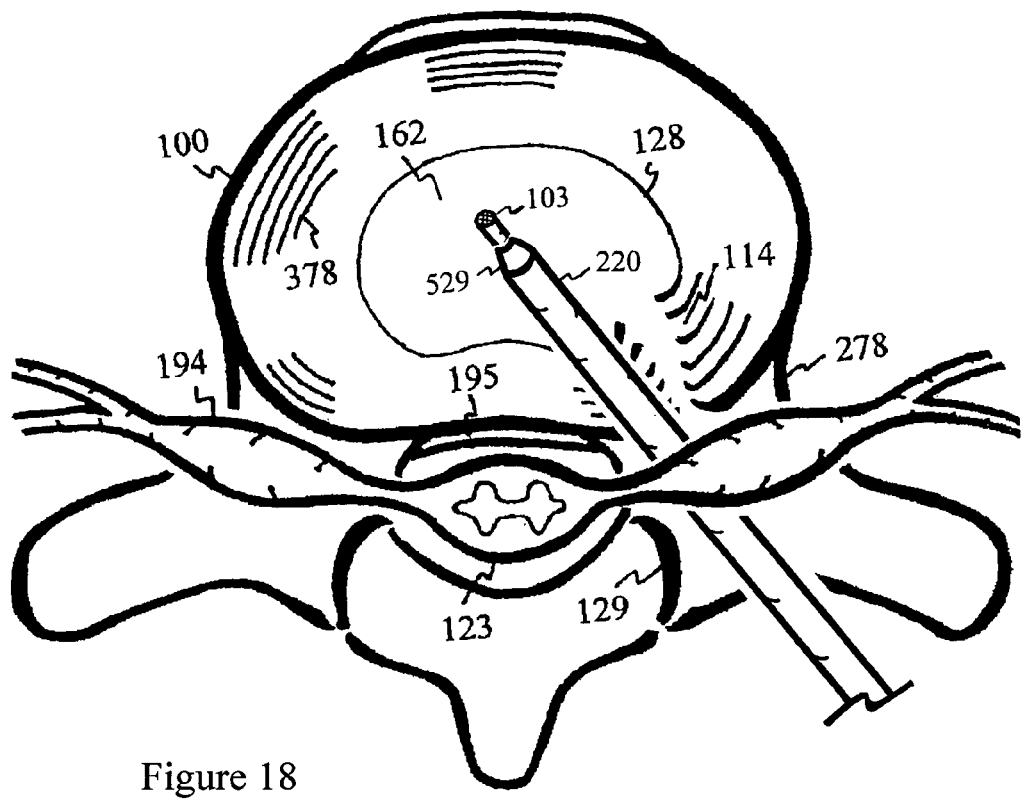
FIG. 18 shows replacing the spinal needle 102 with a cone head 529 dilator 220.
Figure 19:
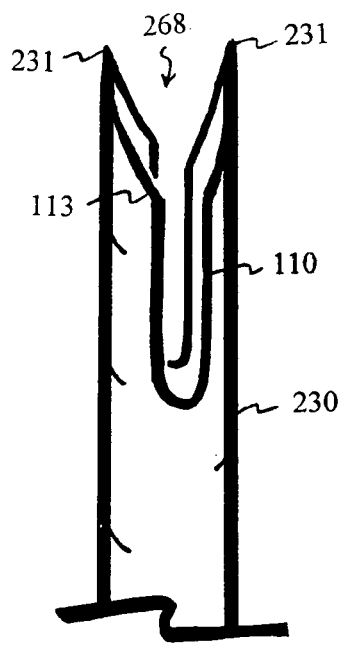
FIG. 19 shows snagging points 231 at the distal end of a cannula 230.
Figure 20:
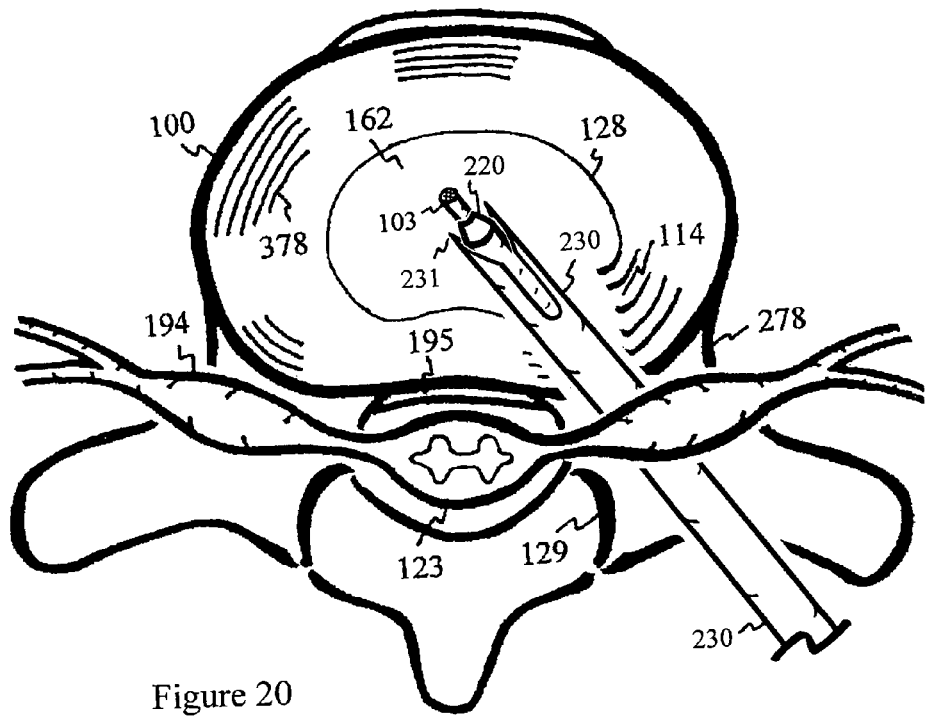
FIG. 20 shows insertion of the cannula 230 sliding over the dilator 220.
Figure 21:
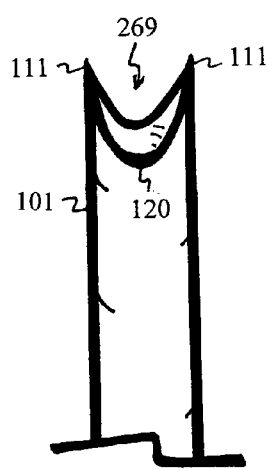
FIG. 21 shows a filament needle 101 with at least one filament gripper 111.
Figure 22:
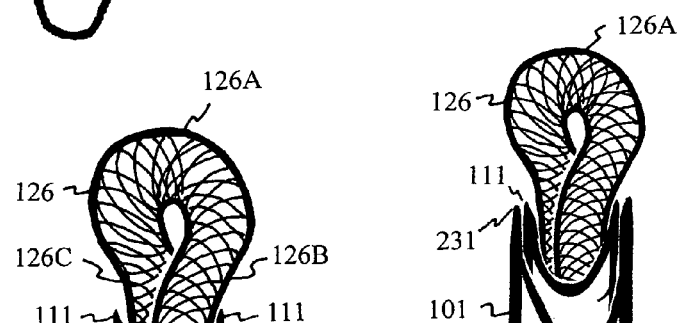
FIG. 22 shows a U-shaped filament 126 with the U-portion or distal portion 126A extended from the filament needle 101.
Figure 23:
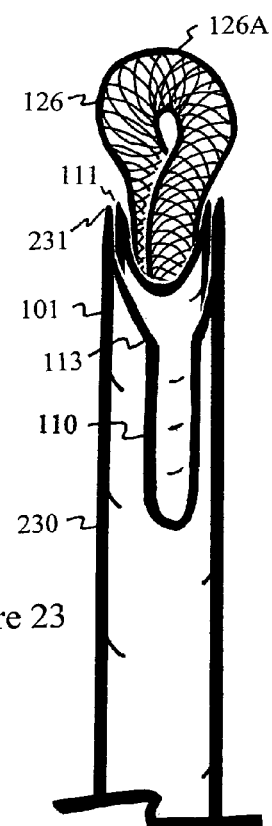
FIG. 23 shows insertion of the filament needle 101 with filament 126 into the cannula 230.
Figure 24:
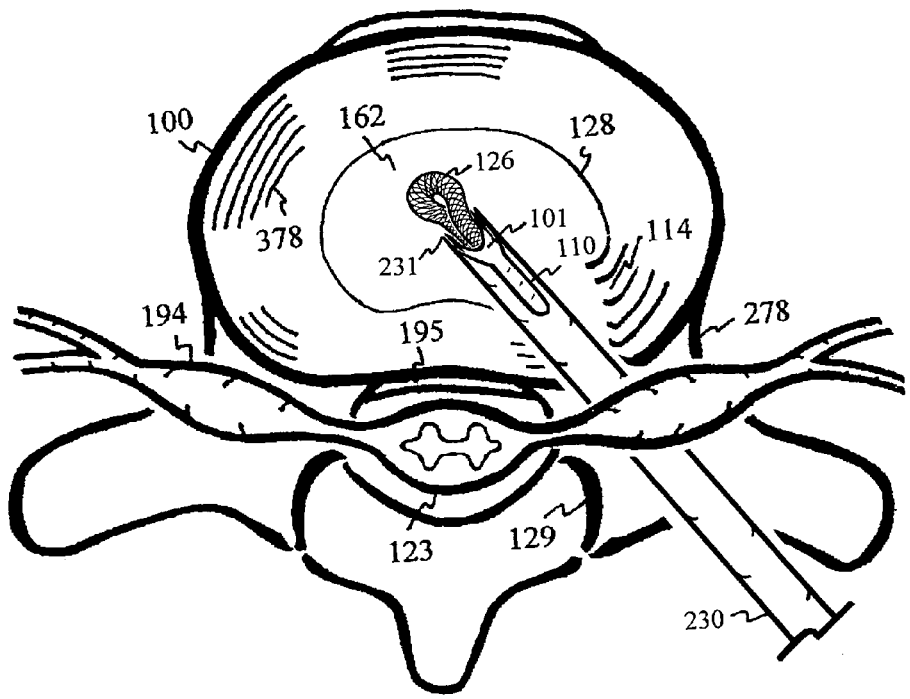
FIG. 24 shows the dilator 220 in FIG. 20 is replaced by the cannula 230 and needle 101.

After confirming discogenic pain with discography, the needle 102 is advanced into the painful disc 100 over the small spinal needle 460, in FIG. 16. The small spinal needle 460 is replaced with a blunt guide wire 103 in the spinal needle 102 into the disc 100, in FIG. 17. The proximal end of the guide wire 103 is held stationary during withdrawal of the spinal needle 102 from the patient. The proximal end of the guide wire 103 is also held stationary to slide a dilator 220 with a blunt cone head 529 over the guide wire 103 into the disc 100 or tissue, as shown in FIG. 18. A cannula 230 has at least one snagging point 231 and longitudinal lumen 268, as shown in FIG. 19. The snagging point 231 can also be a sharp edge 231 with filament gripping or catching capability. The cannula 230 can have a window 110 opened to the lumen 268 and distal opening. While the proximal end of the dilator 220 is held stationary, the cannula 230 is advanced, sliding over the dilator 220 into the disc 100, as shown in FIG. 20. The guide wire 103 and dilator 220 are removed. A filament needle 101 contains at least one gripper 111 and a longitudinal lumen or opening 269 as shown in FIG. 21. Distal end 126A of a filament 126 is extended from the needle lumen 269, as shown in FIG. 22. The distal end 126A of the filament 126 can be U-shaped. The filament needle 101 with the filament 126 is inserted into the lumen 268 of the cannula 230 into the disc 100, as shown in FIGS. 23-24. A funnel 492 in the proximal end of cannula handle 132 in FIG. 26 is used to facilitate insertion of the filament needle 101 of FIG. 22 into the proximal opening of cannula 230.

Figure 25:
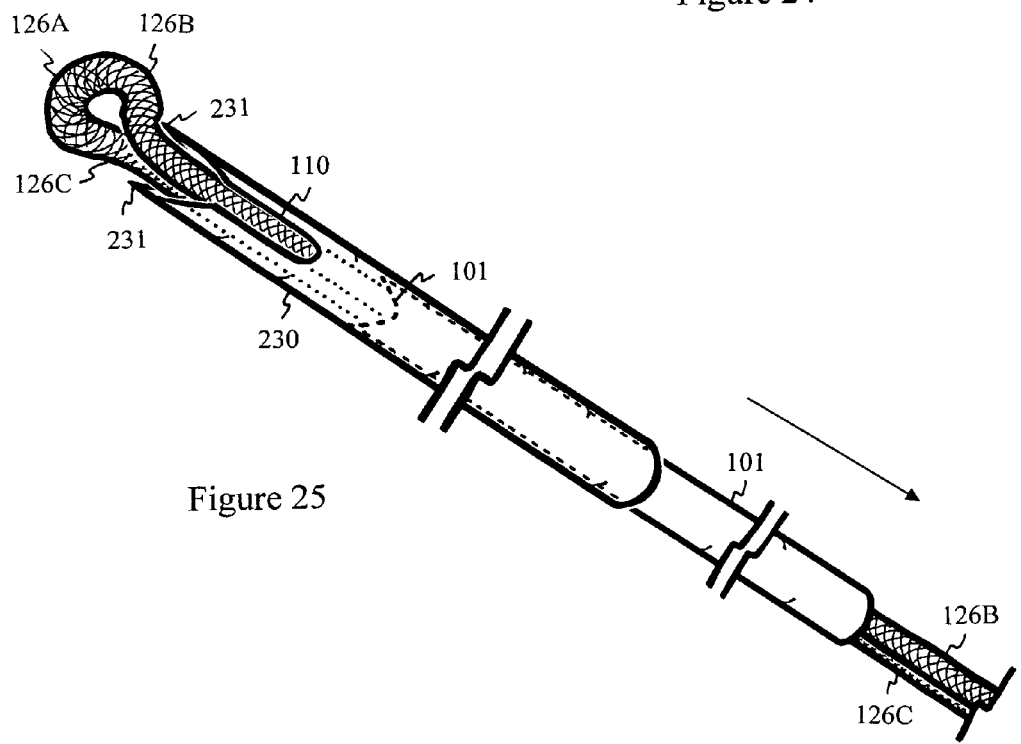
FIG. 25 shows the snagging point 231 of the cannula 230 snags the filament strand 126B during partial withdrawal of the needle 101 to deposit a section of filament 126B, 126C in cannula 230 between distal ends of cannula 230 and needle 101.

During partial withdrawal of the filament needle 101 into the cannula lumen 268, the distal portion 126A or extended portion of the filament 126 is snagged, caught, hooked, retained, trapped, held or grabbed by the snagging point 231 in FIG. 25. As a result, the distal portion 126A or extended portion of the filament 126 remains outside in contact with surrounding tissue in front of the distal end of the cannula 230; and a section of filament 126B, 126C is deposited in the lumen 268 of cannula 230 between the distal ends of the cannula 230 and needle 101. A bobbin 152 holding a spool of filament 126 is fastened at the proximal end of a needle handle 130, as shown in FIG. 26. During snagging or holding of the distal portion 126A of the filament 126 and partial withdrawal of the needle 101, additional filament 126 from the bobbin 152 feeds into the lumen 269 of the needle 101. The needle 101 is re-advanced from FIG. 25, pushing or expelling the deposited filament 126B, 126C in front of the needle 101 out the cannula 230 into tissue, as shown in FIGS. 27-28. Excessive withdrawal of the filament needle 101 will deposit a long filament 126B, 126C in front of the filament gripper 111 of the needle 101 within the cannula 230. The long filament 126B, 126C within the cannula 230 can jam the re-advancing needle 101. A latch 495 on a flexible spring or nitinol wire 494 extends from a cannula handle 132 to limit and prevent excessive length or distance of partial withdrawal of the filament needle 101 by stopping the proximal protruded end 501 of the needle handle 130. Hence, length of filament 126B, 126C deposited within the cannula 230 from partial withdrawal of needle 101 is short enough to be pushed or expelled out the cannula 230 by re-advancement of the filament needle 101, as shown in FIGS. 27 and 28. The deposited filament 126B, 126C may also exit through the window 110 of the cannula 230 in FIGS. 19 and 27 to avoid jamming during re-advancement of the needle 101. During insertion of the filament needle 101 in FIG. 22 through the funnel 492 leading into the lumen 268 of the cannula 230, the needle handle 130 slides over the slope 496 of the latch 495 for filament 126 spiraling. FIG. 26 shows a marker 493 on the needle 101. Distal ends of both filament needle 101 and cannula 230 are even, as shown in FIG. 23 or 27, when the marker 493 lines up at the opening of the funnel 492. When the marker 493 enters into the funnel 492, the grippers 111 of the needle 101 are extended outside the cannula 230 to push and pack the filament 126 into tissue.

Major blood vessels, abdominal aorta, inferior vena cava and common iliac arteries, are anterior to the lumbar discs. Distal ends of the devices must remain within the discs 100, confirmable by fluoroscope (X-ray) or markers on the devices to minimize intermittent X-ray exposure to patients and physicians. Markers on proximal ends of the guide wire 103 and dilator 220 help physician to identify device orientation. The following table shows lengths and markers on sequential devices to guide implantation of spiraled filament 126 into disc 100 to relieve back pain. Markers in the table are measured from the distal end of the device. For safety of the patient, length of a guiding device is preferred to be longer than the subsequent device, so that the proximal end of the guiding device can be held stationary during insertion of the subsequent device into patient.

| Device | OD, mm | ID, mm | Length, mm | Marker 1, mm | Marker 2, mm |
|---|---|---|---|---|---|
| Spinal needle 102 | 1.27 | 0.84 | 172 | | |
| Small spinal needle 460 | 0.51 | 0.25 | 226 | | |
| Guide wire 103 | 0.81 | | 492 | 172 | 338 |
| Dilator 220 | 1.83 | 1.00 | 338 | 185 | |
| Cannula 230 | 2.41 | 1.97 | 185 | | |
| Filament needle 101 | 1.83 | 1.52 | 230 | 185 | |
| Filament 126 | 0.67-0.77 | | 900 double strands | | |

Figure 17:
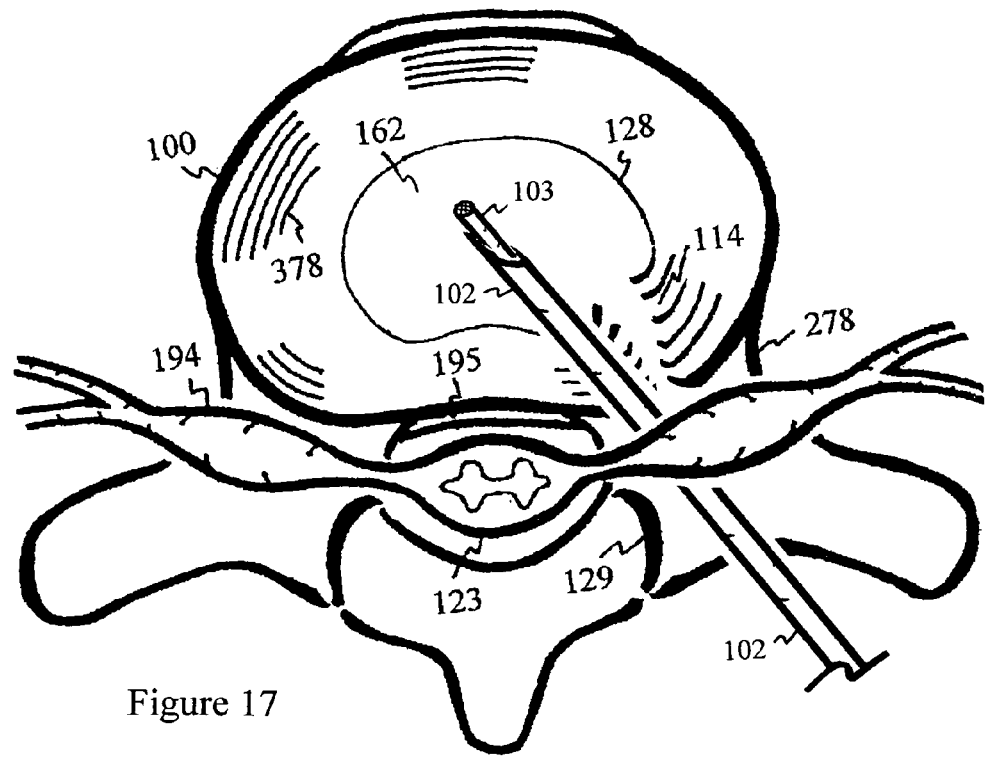
FIG. 17 shows replacing the small spinal needle 460 with a guide wire 103.

Distal ends of spinal needle 102 and guide wire or tube 103 are even, when Marker 1 of the guide wire 103 is at the proximal end of the spinal needle 102, as shown in FIG. 17. Distal ends of the dilator 220 and guide wire 103 are even, when Marker 2 of the guide wire 103 is at the proximal end of the dilator 220, as shown in FIG. 18. Distal ends of cannula 230 and dilator 220 are even, when Marker 1 of the dilator 220 is at the proximal end of cannula 230, as shown in FIG. 20. Distal ends of the cannula 230 and filament needle 101 are even, when Marker 1 of the needle 101 is at the proximal end of the cannula 230, as shown in FIG. 24.

Annulus 378 of the disc 100 is made mainly with layers of collagen. Layers of collagen form a net-like matrix. Spinal needles 102 or 460 with single sharp tips have no problem puncturing through the net-like collagen matrix of the annulus 378. On the other hand, the cannula 230 and filament needle 101 have multiple sharp points 231, 111 at the distal ends, as forks. The cannula 230 contains indentations 113 between snagging points 231 in FIG. 19; and filament needle 101 contains indentations 120 between grippers 111 in FIGS. 21-22. The indentations 113, 120 are trapped by the net-like collagen matrix with no annular penetration capability to prevent possibility of injuring blood vessels anterior to the discs 100. The guide wire or tube 103 and dilator 220 are blunt and have little capability of penetrating annulus 378 to ensure safety of the patient.

Figure 29:
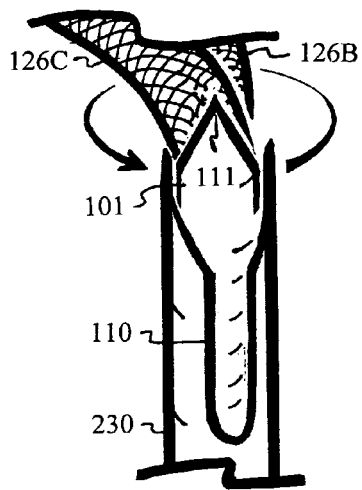
FIG. 29 shows gripping of the filament 126 by the gripper 111 of the rotating needle 101.
Figure 30:
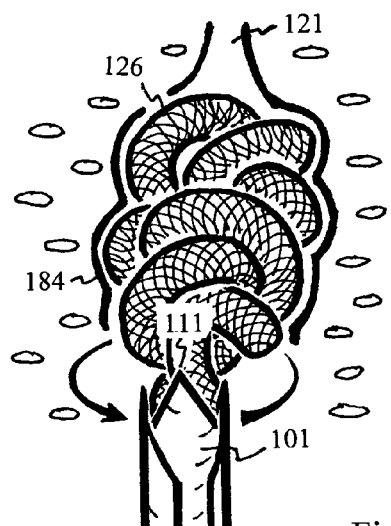
FIG. 30 shows the needle 101 driving the filament 126 to spiral and burrow into tissue, void 184 or fissure 121.
Figure 31:
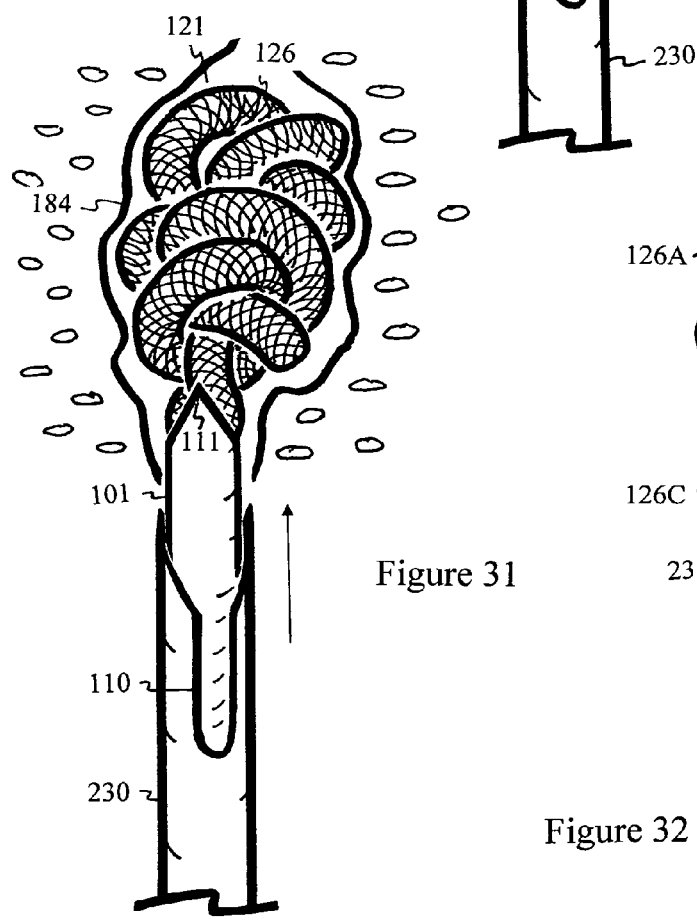
FIG. 31 shows pushing of the needle 101 to pack and burrow the spiraled filament 126 into tissue, void 184 or fissure 121.
Figure 32:
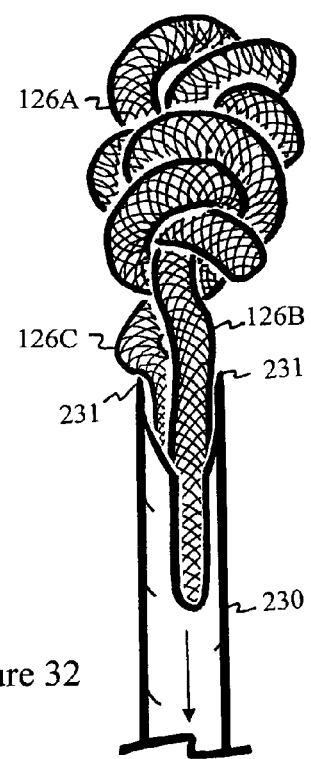
FIG. 32 shows snagging of the filament 126 by the snagging point 231 during withdrawal of the filament needle 101 to deposit additional filament 126B, 126C between distal ends of cannula 230 and needle 101.
Figure 33:
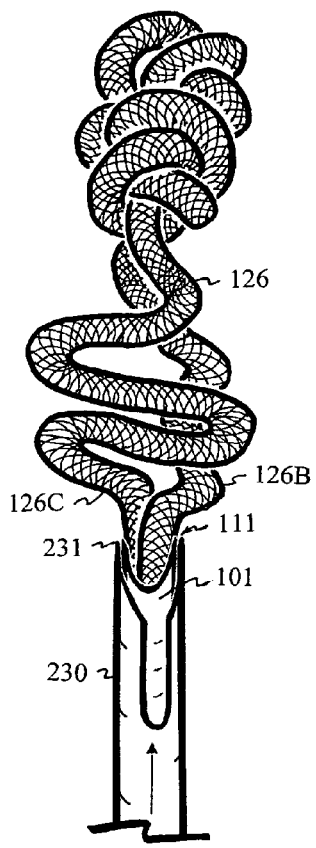
FIG. 33 shows another re-advancement of the filament needle 101, pushing the additional deposited filament 126B, 126C out of the cannula 230 into tissue.
Figure 34:
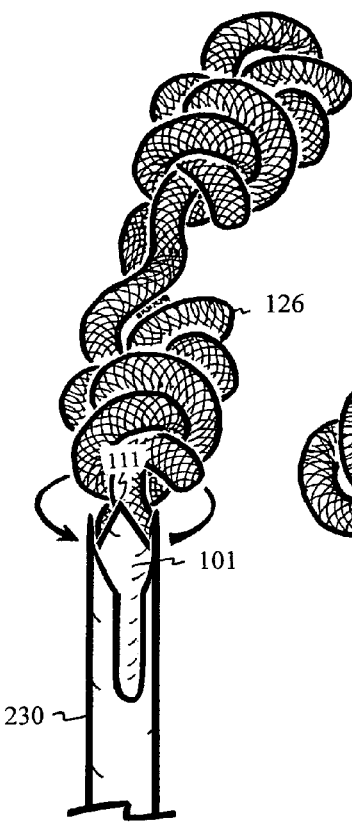
FIG. 34 shows the needle 101 driving the filament 126 to form another spiral, burrowing into tissue with previously spiraled filament 126.
Figure 35:
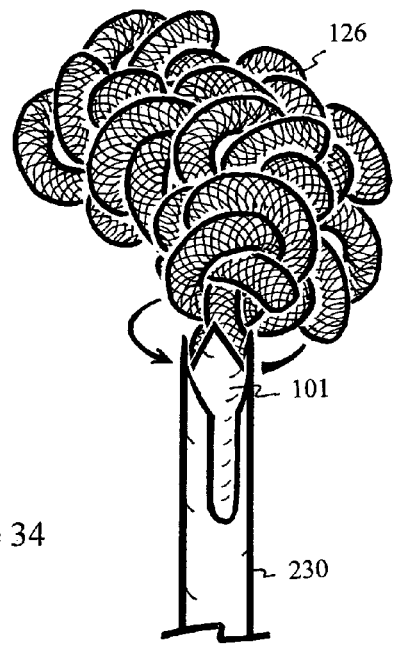
FIG. 35 shows repeated steps of withdrawal, re-advancement, rotation and pushing of filament needle 101 to form multiple spiraled filaments 126 to bulk, fill or fortify tissue.
Figure 36:
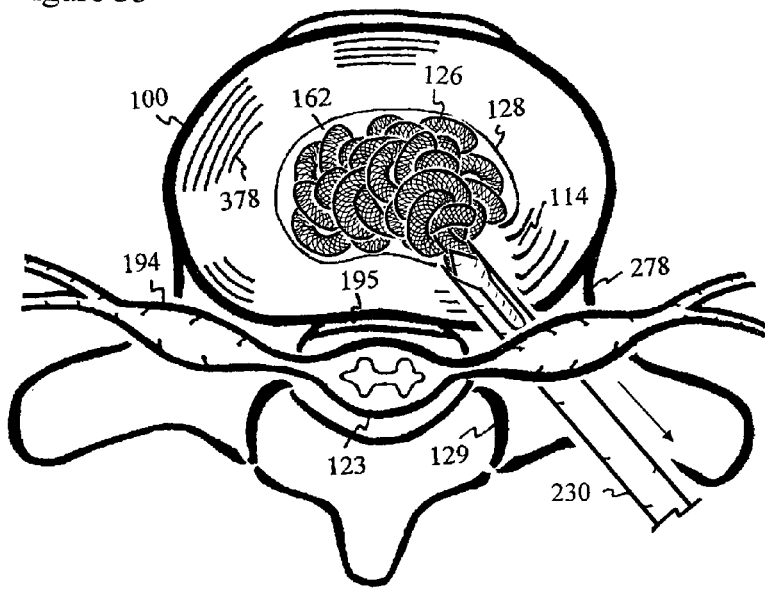
FIG. 36 shows withdrawal of the cannula 230 and needle 101 after packing the nucleus 128 of degenerated disc 100 with spirals of filaments 126.

During pushing and rotation of the filament needle 101, at least one of the grippers 111 grabs and spins the extended filament 126B, 126C burrowing and spiraling into nucleus 128, fissure 121, void 184 or soft tissue, as shown in FIG. 29. Spiraling of the extended filament 126 is made possible by the twisting gripper 111 and friction between the extended filament 126 and tissue. A knot-like spiraled filament 126 is formed due to rotation of the filament needle 101, as shown in FIG. 30. The filament needle 101 can also advance or extend beyond the distal end of the cannula 230 to push, pack, fill, load, cram or stuff the expelled filament 126, burrowing into nucleus 128, void 184, fissure 121 or tissue, as shown in FIG. 31. The filament needle 101 is partially withdrawn again; the extended filament 126 is caught again by the snagging point 231 of the cannula 230, as shown in FIG. 32. In fact, the initial spiraled filament 126 also acts as an anchor outside the distal end of the cannula 230; partial withdrawal of the needle 101 deposits or loads additional filament 126B, 126C within the cannula 230 between distal ends of cannula 230 and needle 101. The filament needle 101 is re-advanced, pushing or expelling the additional filament 126 out of the cannula 230 into tissue 31, as shown in FIG. 33. Rotations of the needle 101 form another spiraled filament 126, linking to the previously spiraled filament 126, as shown in FIG. 34. Same direction of needle 101 rotations is preferred. Rotation and pushing of the needle 101 help the spiraled filament 126 to seek, burrow and fill void 184, gap, fissure 121, vacancy, weak spot, opening, cavity or soft spot. The steps of needle 101 withdrawal, re-advancement, rotation and pushing, are repeated to build, fill, bulk, pack, fortify, load or solidify the tissue with multiple inter-connecting spirals of filament 126, as shown in FIGS. 35-36. Multiple spirals or coils of filament 126 are formed, packed or inserted individually to be shape conforming, malleable and/or resilient in voids 184, yet inter-connected to prevent or minimize migration from tissue. Rotation and pushing of the needle 101 drive the spirals of filament 126 from the lumen 269 of the needle 101 to seek, fill and pack the distal, lateral and/or proximal space in tissue. The spirals of filament 126 are remained and probably formed in multiple axes. Tightness of the spiraled filament 126 is determined by number of rotations and intensity of pushing of the needle 101. The spiral filament 126 can be as tight as a suture knot. Fewer rotations and/or gentle pushing of the needle 101 make soft spirals of filament 126. Number of rotations and pushing intensity of the needle 101 can be alternate to allow variations in firmness or density of filament spirals 126 within repaired tissue. It is possible to sequential withdraw the cannula 230 from tissue to provide additional distal space for packing additional spirals of filament 126.

Figure 37:
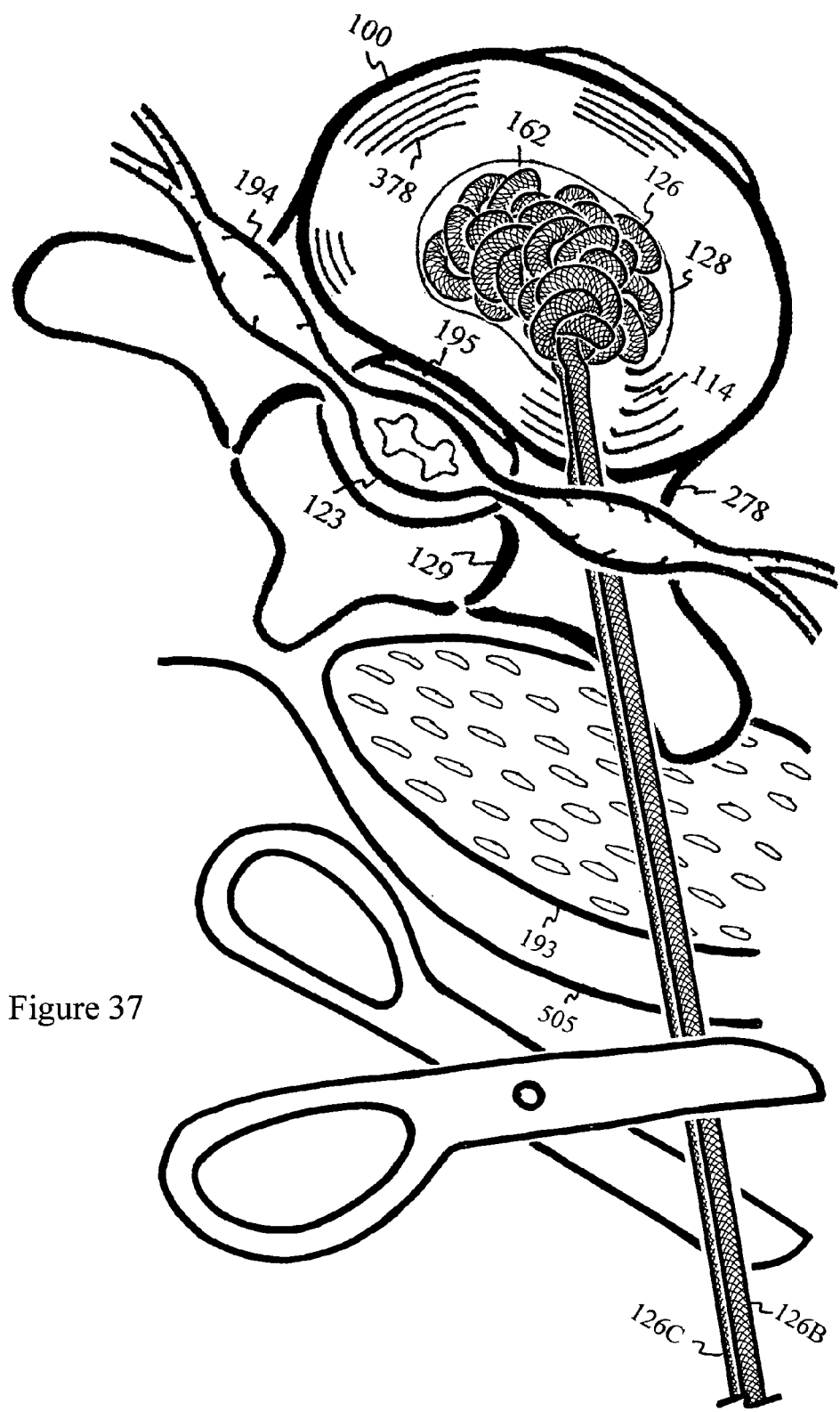
FIG. 37 shows cutting of the filament 126 near the skin 505.
Figure 38:
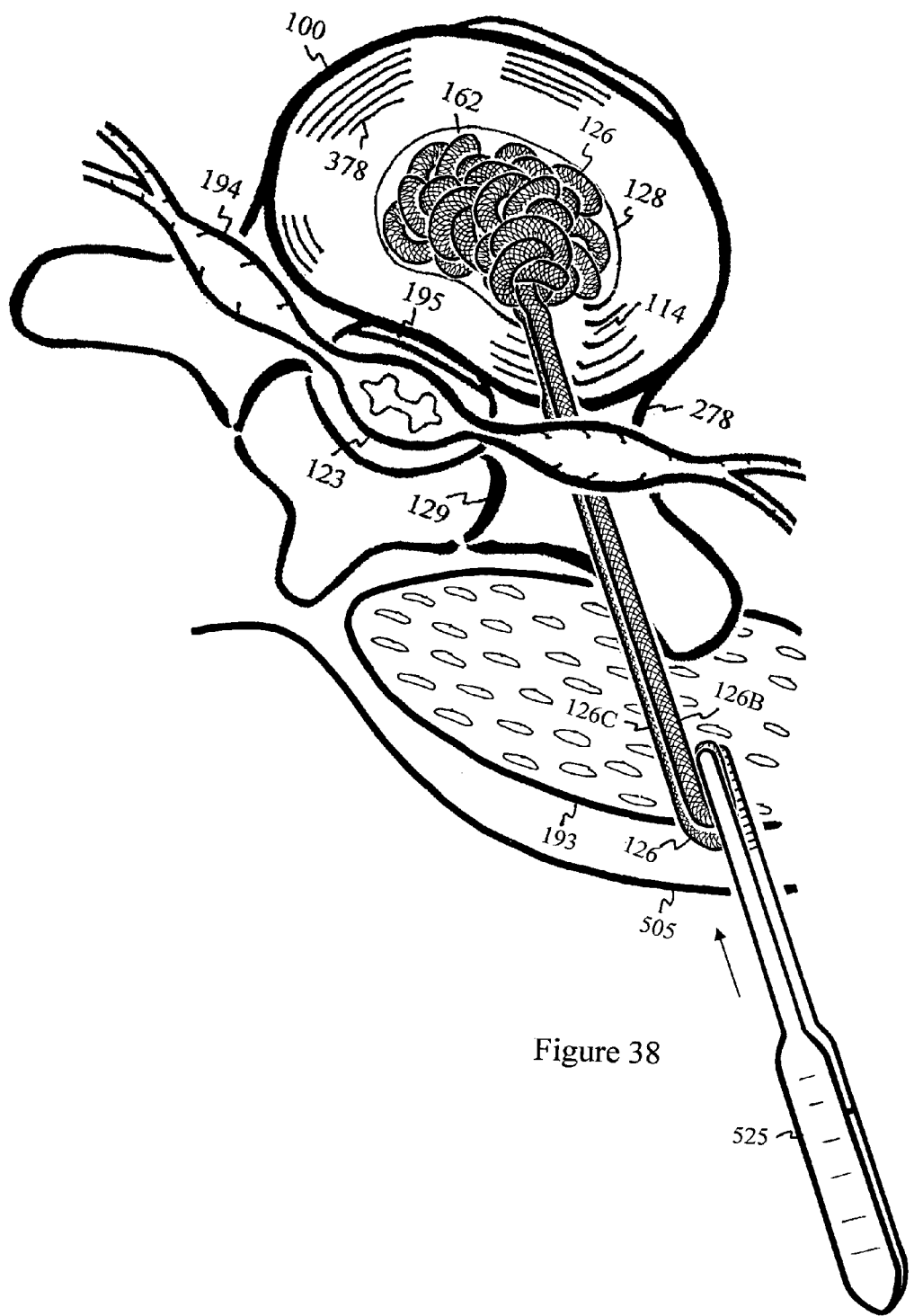
FIG. 38 shows tucking of the filament 126 beneath skin 505 with a long-thin forceps 525.

Needle handle 130 and cannula handle 132 are dumbbell shape. The needle handle 130 has a protruded proximal end 501 and a protruded distal end 500 to facilitate withdrawal and advancement of the needle 101, as shown in FIG. 26. The needle handle 130 also contains gripping or friction ridges 502 to facilitate rotation of the needle 101. The cannula handle 132 has a protruded proximal end 499 and a protruded distal end 498 to facilitate withdrawal and advancement of the cannula 230. When the tissue is full with spirals of filament 126, advancement of the needle 101 becomes difficult. The cannula 230 can also be slightly and sequentially withdrawn from tissue, to pack or accumulate additional spirals of filament 126 distal to the cannula 230. A metering device can be attached to the spool of filament 126 on the bobbin 152 to monitor length of filament 126 dispensed into patient. When the tissue is packed with spirals of filament 126, the filament needle 101 and cannula 230 are withdrawn from tissue. In the event of disc 100 repair, the extended filament 126 is cut above the skin 505, as shown in FIG. 37. The proximal portions of filament 126B, 126C are tucked beneath the skin 505 with a long and thin forceps 525, as shown in FIG. 38. The amount of implanted filament 126 is selectable, controllable, limitable or regulateable by the physician.

In summary, the cannula 230 and filament needle 101 work together to spiral the filament 126 or shunt 126 bulking the tissue. The stationary cannula 230 with snagging points 231 prevents the extended filament 126A from retrieving or retracting into the lumen 269 of the filament needle 101. Additional filament 126 is advanced by either withdrawal/re-advancement of the needle 101 or by a filament advancer 526 within the needle 101. Rotation of the needle 101 with grippers 111 holds and spirals the filament 126 burrowing into voids 184 and fissure 121. The filament spiral 126 is individually formed by spatial allowance of the tissue, and not spiraling over a spindle, axle, axis or needle. Filament 126 spiraling driven by the rotating needle 101 is space seeking, filling, fitting or conforming to fortify, bulk, fill, cushion or repair the tissue. Pushing of the needle 101 further packs the spiraled filament 126 to bulk the tissue.

PCT/US2011/000007, WO/2011/082390 (Internal and external disc shunts alleviate back pain, by Jeffrey E. Yeung and Teresa Yeung, filed on 3 Jan., 2011) contains a U-shaped shunt 126 partly within and partly outside a needle 101, and a sleeve 220 sliding over the needle 101. During rotation of the needle 101, the outside draping shunt 126 spirals over the needle 101 shaft. The sleeve 220 is then advanced distally to strip the spiraled shunt 126 off the shaft of the needle 101, pushing the spiraled shunt 126 into the nucleus of the intervertebral disc 100. The sleeve 220 is retrieved to the proximal position. Another spiral of shunt 126 is formed by rotation of the needle 101, the sleeve 220 is advanced again to strip the spiraled shunt 126 off the needle 101 into the nucleus. The process of needle 101 rotation, sleeve 220 advancement and sleeve 220 retrieval are repeated to form spirals of shunt 126 within the disc 100. However, many problems occurred during usages of this device in clinical study. Due to friction between disc 100 and sleeve 220, advancement of the sleeve 220 for stripping the spiraled shunt 126 from the needle 101 is very difficult. Significant force is required to advance the sleeve 220, which adds significant risks of puncturing through the disc 100 and rupturing major blood vessels anterior to the disc 100. In addition, due to direct contact of the sleeve 220 with the painful disc 100, patient feels extreme pain during advancement of the sleeve 220 to dislodge the spiraled shunt 126 on the needle 110. Significant pain is endured during multiple dislodgements of shunt spirals 126. Fortunately, the patient experienced pain relief within a week due to efficacy of the disc shunt 126.

Unlike PCT/US2011/000007, WO/2011/082390, the cannula 230 in this application is stationary during implantation of the filament 126 into disc 100 or tissue. The filament needle 101 slides freely within the cannula 230 without risk to the patient or causing pain. The spiral of filament 126 is driven by the grippers 111 and formed distal to the rotating needle 101, capable of burrowing, drilling, packing, wiggling, building, dilating, wedging or shimming into voids 184, fissure 121 or tissue. Unlike PCT/US2011/000007, tissue burrowing of the distal forming filament spiral 126 in this application is particularly effective, deep, and tight, as shown in FIG. 30, embedding, filling, packing and bulking the tissue as shown in FIG. 36. The spiraled filament 126 in PCT/US2011/000007, WO/2011/082390 is already formed on the needle 101 shaft, which may not fit into small voids 184 or fissures 121. In addition, spiraling of the filament 126 in this application is particularly unique. Filament 126 spiraling can occur only in tissue, interference or friction surrounding the extended filament 126, different from disc shunt 126 spiraling the over the needle 101, as taught in PCT/US2011/000007, WO/2011/082390.

Figure 39:
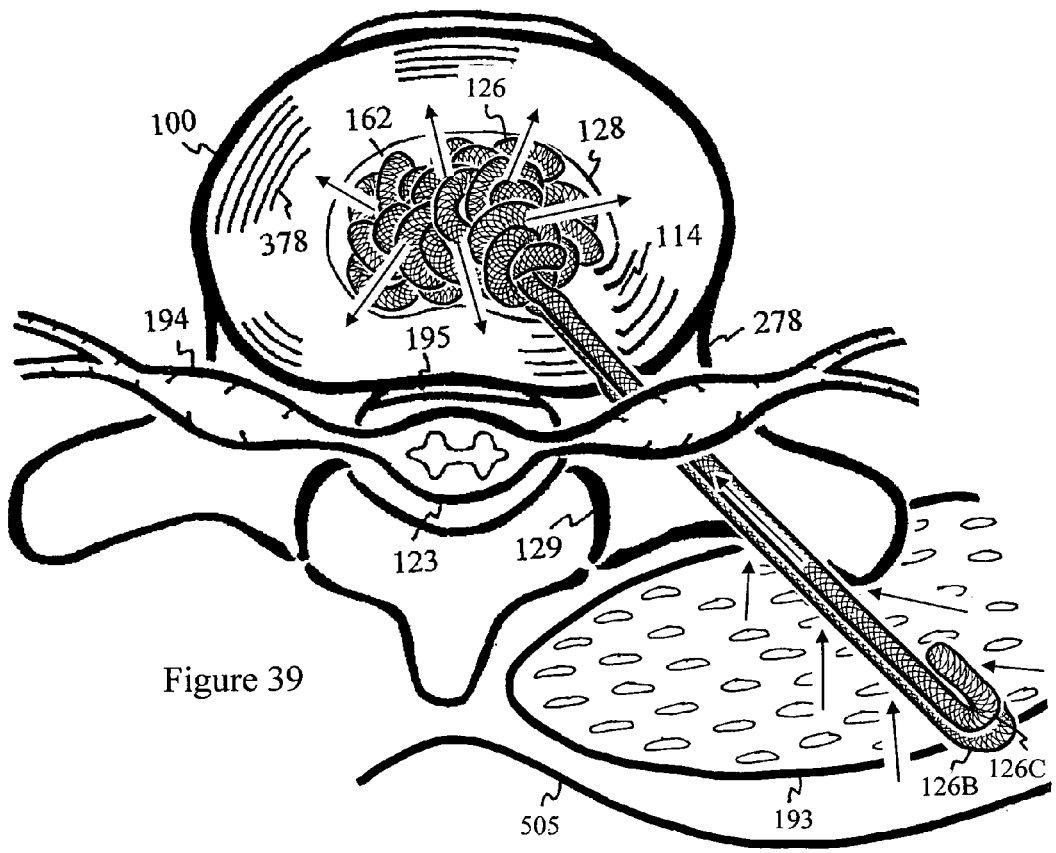
FIG. 39 shows fluid flowing through the filament 126 from low osmotic pressure in muscle 193 to high osmotic pressure in desiccated disc 100.

Fluid flows from low to high osmotic pressure according to the law of physics. Osmotic pressure of blood plasma in muscle 193 is approximately 250-300 mOsm/liter; intervertebral disc 100 is 300-400 mOsm/liter. Through the difference between osmotic pressures, the connecting filament 126 draws fluid from muscle 193 to hydrate the desiccated nucleus 128 without a pump, as shown in FIG. 39.

In-vitro study, the filament 126 was implanted into sheep discs 100 (430 mOsm/liter) and human cadaver discs 100 (300-400 mOsm/liter) of various degenerative levels, Thompson Grade 0-4. The discs 100 with filaments 126 were submerged in saline with blue dye (300 mOsm/liter). Dissection of the discs 100 showed blue saline permeation into the nuclei 128, confirming fluid flows from low to high osmotic pressure.

Another filament 126 was implanted through a muscle into a sheep disc 100. The sheep muscle 193 was saturated with iopamidol (contrast agent with blue dye, 545 mOsm/l). The blue iopamidol did not permeate through the filament 126 into the sheep disc 100 (430 mOsm/liter). In fact the dissected disc 100 looked desiccated; fluid within the sheep disc 100 was probably drawn into the muscle 193 infused with 545 mOsm/liter blue iopamidol through the filament 126. The experiment was repeated with diluted blue iopamidol solution (150 mOsm/liter). The diluted iopamidol solution saturated the muscle 193 and permeated through the filament 126 into the sheep disc 100 visible and traceable from muscle 193 to nucleus 128 under CT. Dissection confirmed permeation of the diluted blue iopamidol into the nucleus 128 of the sheep disc 100. Again, fluid flows from low to high osmotic pressure through the filament 126.

Sheep discs were implanted with filaments 126 and submerged in pork blood (about 320 mOsm/liter). Dissection of the discs 100 showed permeation of pork blood through the filament 126 into the nuclei of the sheep discs 100 (430 mOsm/liter).

Figure 40:
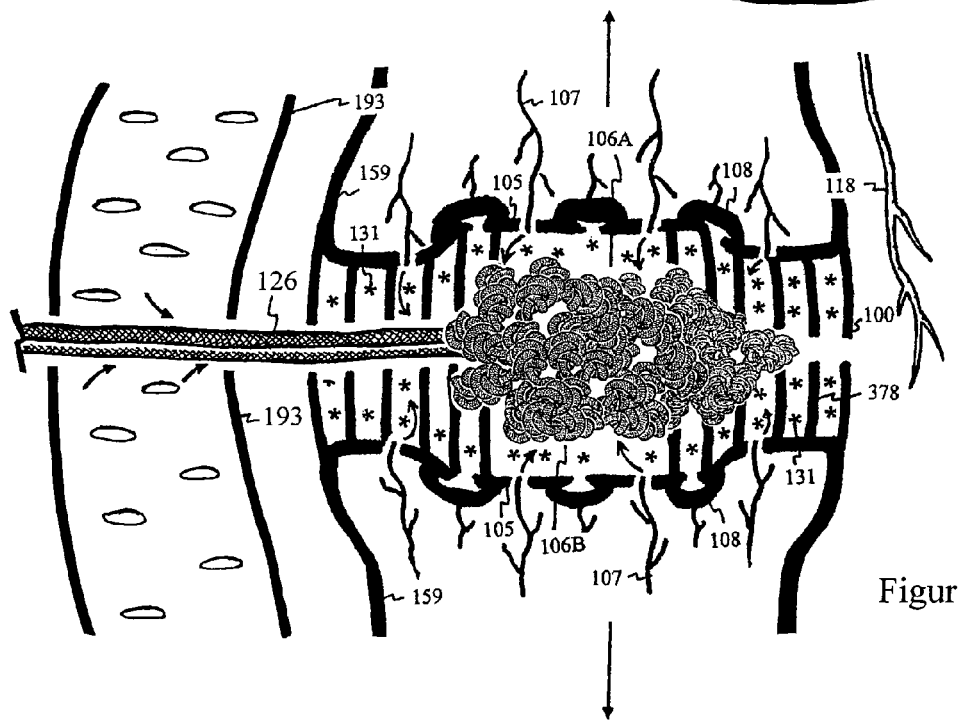
FIG. 40 shows a longitudinal view of a disc 100 filled with spiraled filament 126, wicking fluid from muscle 193, superior 106A and inferior 106B diffusion zones into mid layer of disc 100.

Gradient of pH is formed in the disc 100 due to shallow diffusion of pH buffer 131 from the capillaries 107 at the endplates 105. The superior 106A and inferior 106B diffusion zones are approximately 0-2 mm from the superior or inferior endplates 105. The pH in the superior 106A and inferior 106B diffusion zones is neutral. Acidity increases at the mid layer of the disc 100, where chronic deprivation of oxygen, nutrients and pH buffer occurs. FIG. 40 shows a longitudinal view of a filament 126 filled disc 100 with calcified layers 108 accumulated over the endplate 105. The hydrophilic spiraled filament 126 reaches, locates, resides or contacts at least one of the superior 106A and inferior 106B diffusion zones, drawing and transporting nutrients/oxygen/pH buffer 131 to neutralize lactic acid 162 and nourish cells in the mid layer of the disc 100. As a result, lactic acid 162 burn is minimized and back pain is relieved. In essence, the spiraled filament 126 bridges, links or transports fluid between source of oxygen/nutrients/pH buffer 131 and mid layer of the disc 100 to treat the etiology and symptom of back pain. Furthermore, oxygen 131 from the muscle 193, superior 106A and inferior 106B diffusion zones converts anaerobic conditions into aerobic within the mid layer of the disc 100 to further reduce production of lactic acid 162 and relieve back pain.

The filament 126 can be further identified as internal filament 126 and external filament 126. The filament 126 in the disc 100 can be called the disc shunt 126 to form as internal shunt 126 between superior diffusion zone 106A and inferior diffusion zone 106B. The disc shunt 126 extending from disc 100 to body circulation or muscle 193 is called external shunt 126. The disc shunt 126 is a fluid-transferring or delivery device, inserted into the nucleus 128 of a degenerated disc 100. Due to relaxation and compression of the disc 100 from daily activities of the patient, spiraled internal shunt 126 in the disc 100 facilitates transport of oxygen/nutrients/pH buffer 131 through out the disc 100. During relaxation, oxygen/nutrients/pH buffer 131 from diffusion zones 106A, 106B are absorbed by the internal shunt 126, and oxygen/nutrients/pH buffer 131 in muscle 193 are drawn through the external filament 126. During compression, oxygen/nutrients/pH buffer 131 in the shunt 126 are expelled to neutralize lactic acid 162 and fed to disc cells in the mid layer of the disc 100. Essentially, both diffusion zones 106A, 106B are expanded to cover the mid layer or acidic layer of the disc 100. Hence, fluid leaking from the fissure 121 is pH neutral or near pH neutral to alleviate back pain, as shown in FIG. 40. Fluid transport or distribution is made possible by soft and pliable spirals of filament 126 as internal disc shunt 126 with hydrophilic and malleable properties, absorbing and delivering nutrients/oxygen/pH buffer 131 within the avascular disc 100. Fluid flow through the shunt 126 is dynamic and continuous with potential to rebuild disc matrix for disc regeneration.

Nutrients/oxygen/pH buffers 131 are diffused from the capillaries 107 at the endplates 105 into the nutrient-poor avascular disc 100, as shown in FIG. 40. Diffusion is concentration related; solutes move from high to low concentration, from capillaries 107 into diffusion zones 106A, 106B. Withdrawal of nutrients/oxygen/pH buffers 131 by the internal shunt 126 leads to additional diffusion of nutrients/oxygen/pH buffers 131 from capillaries 107 and vascular buds. The net supply of nutrients/oxygen/pH buffer solutes 131 into the disc 100 will increase with implantation of the internal shunt 126 as shown in FIG. 40. Distribution of nutrients/oxygen/pH buffer 131 is expanded by the internal shunt 126 covering or permeating the full-thickness of the intervertebral disc 100 to neutralize lactic acid 162, nourish starving disc cells 277 and rebuild disc matrix to sustain compressive loading of the disc 100.

Depending on severity of the calcified layers 108 covering the capillaries 107 and vascular buds at the endplates 105, the superior 106A and inferior 106B diffusion zones containing nutrients/oxygen/pH buffer 131 are between 0 and 5 mm from the cartilaginous endplates 105. For degenerated and/or painful discs 100, the superior 106A and inferior 106B diffusion zones are likely between 0 and 2 mm from the superior and inferior endplates 105. Hence, the internal disc shunt 126 should reach at least one, but preferably both superior 106A and inferior 106B diffusion zones, between 0 and 3 mm from both endplates. Repetitive formations and deployments of the coiled or spiraled shunt 126 is used to position, reside, locate, reach or contact at least one diffusion zone 106A or 106B, between 0 and 2 mm from at least one endplate 105 to form the internal disc shunt 126. Distance of the internal shunt 126 from the endplate 105 determines availability or quantity of nutrients/oxygen/pH buffer 131 for supplying the mid layer of the disc 100 to alleviate discogenic pain from lactic acid 162 burn.

Due to avascular nature, intervertebral disc 100 is immuno-isolated. In-vivo sheep study, there was no tissue response within the discs 100 to nylon filament 126 after 1, 3, 6, 12 and 30 months, using H&E histology staining. No fibrotic encapsulation over the nylon filament 126 was observed within the discs 100. Similarly, there was no noticeable inflammatory reaction to the nylon filament 126 in a human pilot clinical study in 1 week, 3, 6, 12 and 24 months. Internal transport of nutrients/oxygen/pH buffer 131 from superior 106A and/or inferior 106B diffusion zones continues without hindrance of fibrotic encapsulation over the filament 126 within the intervertebral disc 100.

Figure 41:
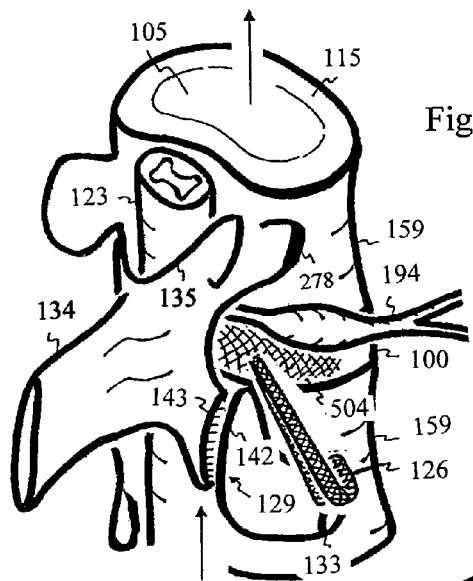
FIG. 41 shows thickening of the filament-packed disc 100 to reduce facet loading and pain by lifting the inferior articular process 143 of the facet joint 129.

The multiple coils or spirals of filament 126 or shunt 126 provide bulk, shimming, filling, cushion, mass, wedging or fortification within the disc 100 to elevate, raise, lift, increase or sustain disc 100 height as indicated by arrows in FIGS. 40-41. Spirals of filament 126 bulk up the nucleus 128 to elevate or support disc height for sustaining axial compression, stiffen the disc 100 for reducing spinal instability, and/or lift the inferior articular process 143 of the facet joint 129 to reduce facet pain, as shown in FIG. 41.

Figure 42:
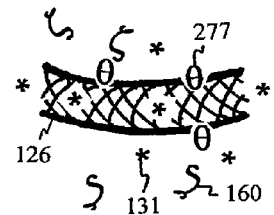
FIG. 42 shows production of biosynthetic molecules 160 or disc matrix by cells 277 receiving nutrients, oxygen and pH buffer 131 transported through the filament 126.

Nutrients/oxygen/pH buffer 131 transported through the filament 126 feed cells 277 to produce biosynthetic molecules, which can be glycosaminoglycans, collagen or disc matrix, as shown in FIG. 42. Cells 277 and nutrients/oxygen/pH buffer 131 can be intradiscally injected, in FIG. 43, to expedite disc 100 regeneration and pain relief.

Figure 44:
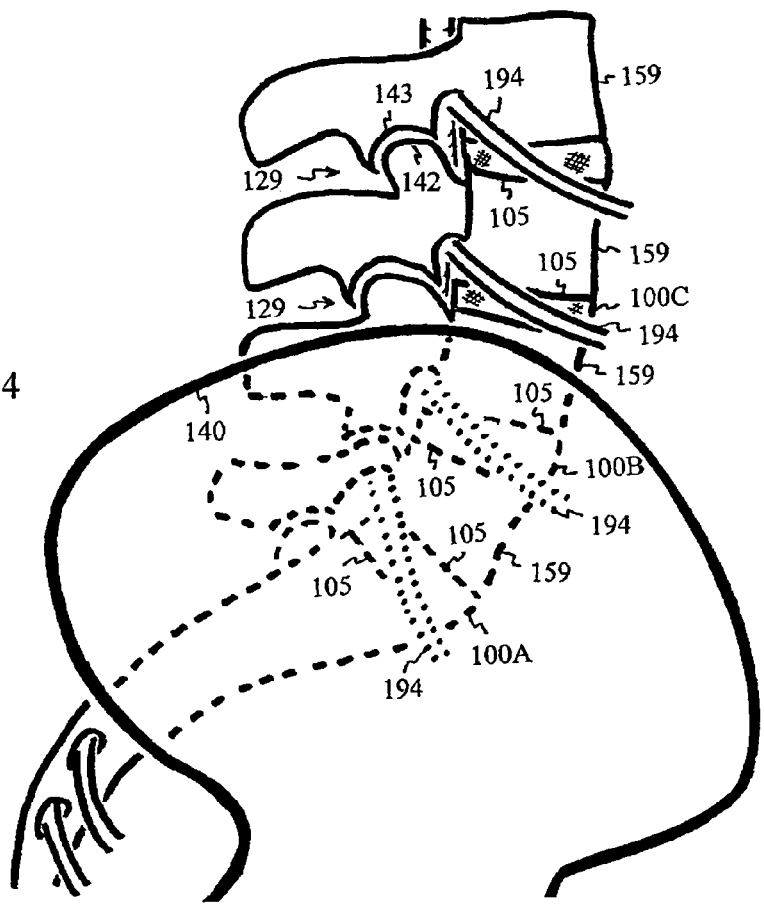
FIG. 44 shows shielding of L5-S1 disc 100A and L4-5 disc 100B by the iliac crest 140, blocking entry of the straight spinal needle 102 of FIGS. 11 and 14.
Figure 45:
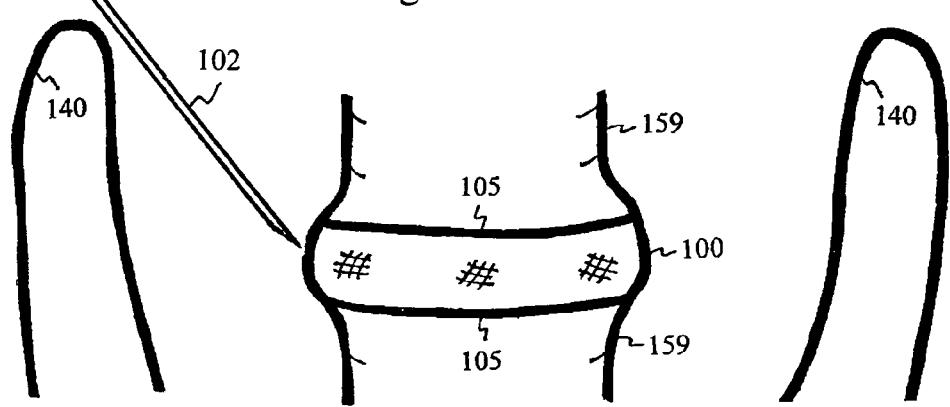
FIG. 45 shows iliac crest blocking of the lower lumbar disc 100, preventing entry of spinal needle 102 into the nucleus of the disc 100.

Lower lumbar L5-S1 disc 100A and L4-5 disc 100B are shielded by a pair of iliac crests 140, as shown in FIG. 44. The straight spinal needle 102 enters superiorly over the iliac crest 140 at an angle, as shown in FIG. 45, difficult or even impossible to deliver the shunt 126 into the nucleus 128 of the disc 100.

FIG. 46 shows an elastically curved cannula 230 leading the filament needle 101 into the nucleus 128 of a degenerated disc 100. The elastically curved cannula 230 is resiliently straightened by sliding over the dilator 220 into the annulus 378 of the disc 100. Then, the dilator 220 is partially withdrawn while holding the cannula stationary. The cannula 230 resumes the curvature and advances into the loosely packed nucleus 128. After confirming distal location of the curved cannula 230 by fluoroscope, the filament needle 101 in FIG. 22 replaces the dilator 220 for filament 126 spiraling, similar to FIGS. 25, 27-39. The cannula 230 and needle 101 can be made with nickel titanium alloy for shaped memory and super elasticity.

In summary, insertion of the spiraled filament 126 into disc 100 increases nutrients/oxygen/pH buffer 131 from muscle 193 and diffusion zones 106A and/or 106B to reduce lactic acid 162 burn and feed cells. The spiraled filament 126 also adds bulk and cushion to reduce spinal instability and facet pain.

The shunt 126 for disc 100 repair is hydrophilic with measurable characteristics under ambient temperature and pressure for transporting and retaining fluid to relieve pain and/or regenerate the degenerated disc 100. After saturation in water, the shunt 126 gains weight between 10% and 500% by absorbing water within the matrix of the shunt 126. A healthy human disc 100 contains 80% water. The preferred water absorbency after water saturation is between 30% and 120%. The shunt 126 can have pore sizes between 1 nano-meter and 500 micro-meters, serving as water retaining pockets or water transporting channels. Pores 124 of the shunt 126 also function as scaffolding or housing for cell 277 attachment and cellular proliferation, as shown in FIG. 42. Water contact angle on the shunt 126 is between 0 and 60 degrees. The preferred water contact angle of the shunt 126 is between 0 and 30 degrees. Height of capillary action for drawing saline up the shunt 126 is between 0.5 and 120 cm. The preferred height of capillary action of drawing saline is between 1 and 60 cm. Height of capillary action for drawing pork blood up the shunt 126 is between 0.5 and 50 cm. The preferred height of capillary action for drawing pork blood up the shunt 126 is between 1 cm and 25 cm. Saline siphoning transport rate through the shunt 126 is between 0.1 and 10 cc per 8 hours in a humidity chamber. Human lumbar disc 100 loses between about 0.5 and 1.5 cc fluid per day due to compression. The saline siphoning transport rate through the shunt 126 is preferred between 0.5 and 5 cc per 8 hours in a humidity chamber. Pork blood siphoning transport rate through the shunt 126 is between 0.1 and 10 cc per 8 hours in a humidity chamber. The pork blood siphoning transport rate through the shunt 126 is preferred between 0.5 and 3 cc per 8 hours in a humidity chamber.

The shunt 126 used in the sheep and human clinical studies have the following physical properties under ambient temperature and pressure: (1) weight gain 80% after water saturation, (2) water contact angle zero degree, (3) height of capillary action 11 cm with pork blood, 40 cm with saline with blue dye, and (4) rate of siphoning pork blood 1.656+/−0.013 cc per 8 hours in a humidity chamber.

Average lactic acid concentration in painful lumbar disc 100 is about 14.5 mM, 15 cc or less in volume (Diamant B, Karlsson J, Nachemson A: Correlation between lactate levels and pH of patients with lumbar rizopathies. Experientia, 24, 1195-1196, 1968). An in-vitro study was conducted to show instant lactic acid neutralization by blood plasma. The spiraled shunt 126 was formed within, and then extracted from a fresh portion of beef. Blood plasma absorbed in the spiraled shunt 126 instantly neutralized 42% of the 14.5 mM, 15 cc of lactic acid solution, measurable by a pH meter.

Approximately 85% back pain patients show no nerve impingement under MRI or CT. A patient without nerve impingement suffered chronic back pain with visual analog score 8-9 out of 10 (most severe), and leg pain with visual analog score 8. Five days after implantation of the shunt 126, the visual analog score dropped to 2.5 for her back pain, but the visual analog score persisted at 8 for leg pain. In the 5.5-month follow-up, the visual analog score dropped to 2.0 for her back pain, and visual analog score dropped from 8 to zero for leg pain. Quick back pain relief may be contributed to instant lactic acid 162 neutralization by blood plasma of the patient to relieve acid burning of the adjacent sensory nerves 118. Leg pain may be caused by acid scaring of the spinal nerve 194 and chemical radiculitis, which takes time to heal and relieve the pain. In human clinical study, the outer diameters of the needle 101 and cannula 230 are only 1.83 and 2.41 mm respectively. The outer diameter of the shunt 126 is 0.55-0.77 mm.

Urinary incontinence is common among women, especially after multiple pregnancies and vaginal deliveries. Major urethral sphincteric action is operated by smooth muscle 532 at the bladder neck 519. FIG. 47 shows a normal and narrow bladder neck 519 of a woman with urinary control. The smooth muscle 532 controls opening and closure of the urethral lumen 517 lined with mucosa 533. During pregnancy, the fetus presses against the bladder 518 and the urethra 516 for months. The downward compression flattens and widens the smooth muscle 532 and urethral lumen 517 of the bladder neck 519, as shown in FIG. 48. A widened lumen 517 at the bladder neck 519 is beyond the range of sphincteric closure of the smooth muscle 532 for coaptation of mucosa 533 in urethral lumen 517. As a result, stress urinary incontinence occurs during increased abdominal pressure from coughing, sneezing, laughing or even standing. In surgical intervention for stress incontinence, the vagina 520 is pulled and fastened to ligaments anteriorly, to support and push forward the posterior wall 524 of the bladder neck 519, narrowing the urethral lumen 517 for coaptation of urethral mucosa 533 during sphincteric action.

Figure 49:
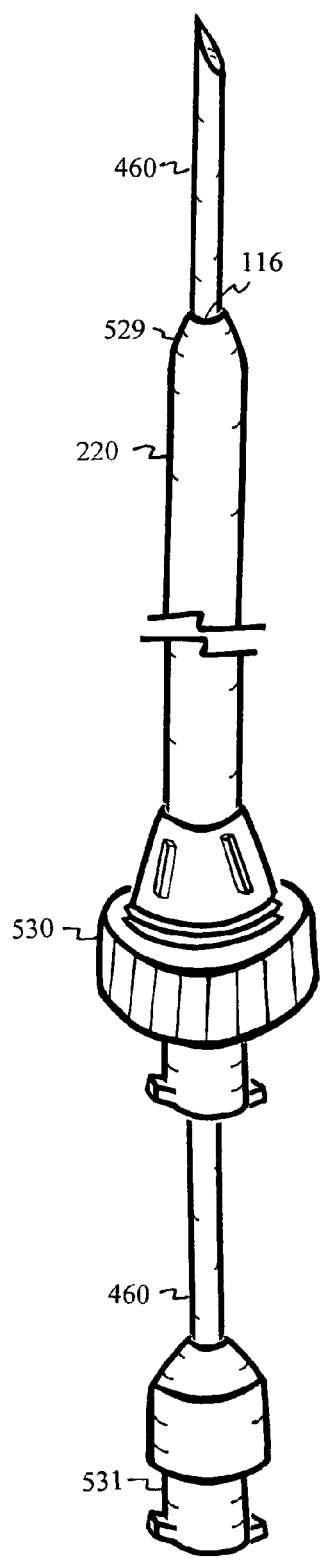
FIG. 49 shows a small spinal needle 460 within a cone-headed 529 dilator 220 fastened by a removable luer lock 530.
Figure 50:
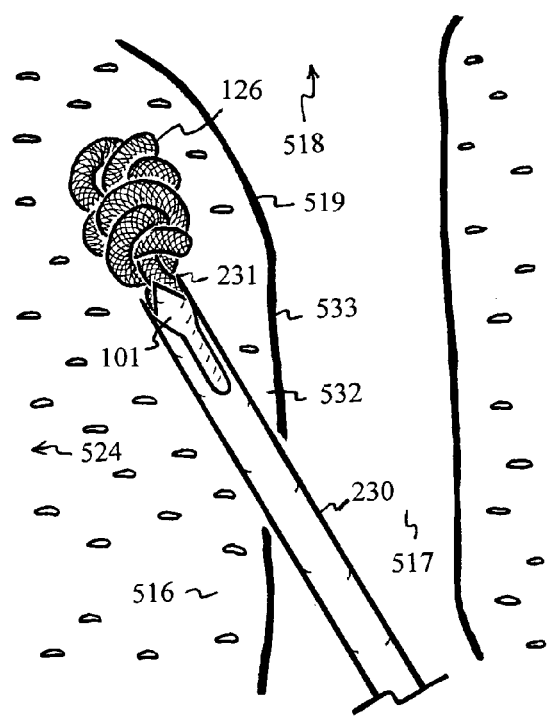
FIG. 50 shows insertion of cannula 230 and needle 101 to implant a spiraled filament 126 in smooth muscle 532 of the bladder neck 519 under cystoscopic or ultrasound guidance.
Figure 51:
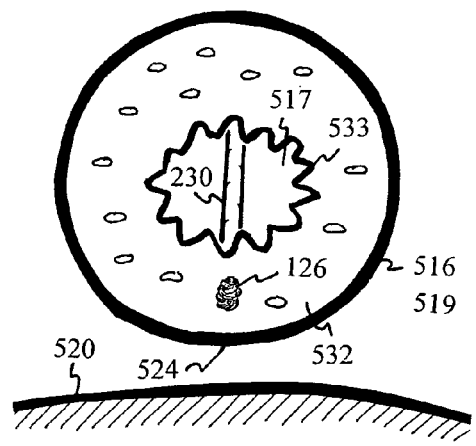
FIG. 51 shows a cross-sectional view of a widened urethral lumen 517 and initial spiral of the filament 126 within the smooth muscle 532 of the urethra 516.
Figure 52:
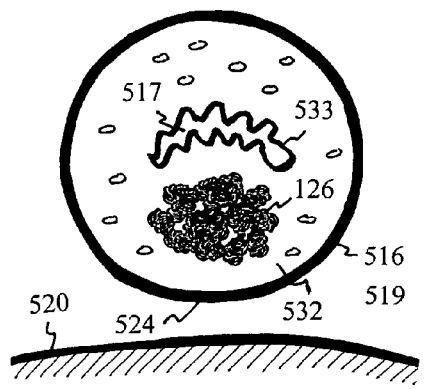
FIG. 52 shows narrowing of the urethral lumen 517 by bulking the urethral smooth muscle 532 with spirals of filament 126 to allow coaptation of urethral mucosa 533.
Figure 53:
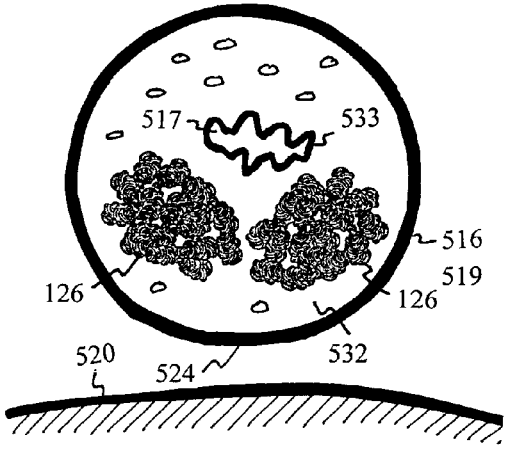
FIG. 53 shows two bulking locations of spiraled filaments 126 to close the urethral lumen 533 and relieve urinary stress incontinence.
Figure 54:
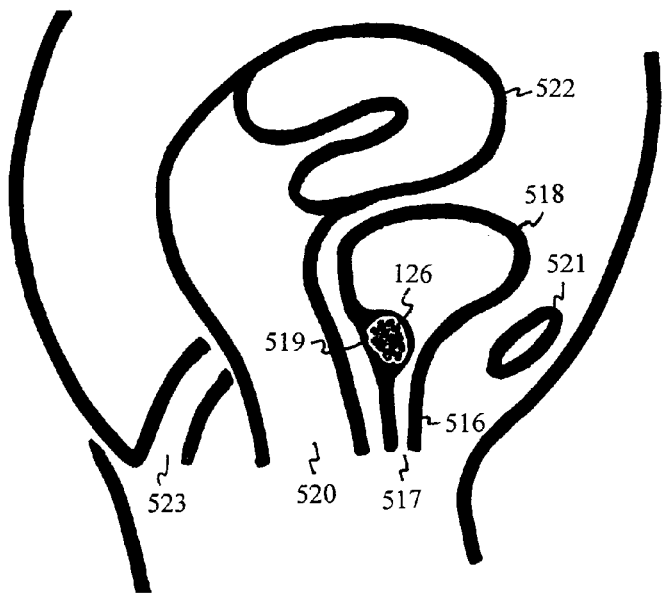
FIG. 54 shows bulking of the urethral smooth muscle 532 with spiraled filament 126, narrowing the urethral lumen 517 at the bladder neck 519 to regain sphincteric control.

A needle 460 within a cone-head dilator 220 in FIG. 49 is inserted into urethral smooth muscle 532 of the bladder neck 519 under cystoscopic or ultrasound guidance. An echogenic gel can be injected through the needle 460 to confirm location of the needle 460 tip within the urethral muscle 532. The cone-head dilator 220 slides over the needle 460 into the urethral muscle 532. The needle 460 is withdrawn. Addition echogenic gel can be injected through the removable luer lock 530 to ensure location of the dilator 220 tip within the urethral muscle 532. The luer lock 530 is removed to prepare for repair. Similar to disc 100 repair, a cannula 230 slides over the dilator 220 into the urethral muscle 532. The dilator 220 is replaced with a filament needle 101 loaded with filament 126 within the cannula 230, as shown in FIG. 23. Spiraled filament 126 in FIG. 50 is created by withdrawal, advancement, rotation and pushing of the filament needle 101, as shown in FIGS. 25, 27 and 29-35. FIG. 51 shows an axial or cross-sectional view of the urethra 516 with a widened urethral lumen 517 and initial spiraled filament 126 formed within the smooth muscle 532 of the posterior wall 524 of the urethra 516. FIG. 52 shows bulking, enlargement or filling of the urethral smooth muscle 532 with spirals of filament 126 at the posterior wall 524 to encroach or extend into the space of urethral lumen 517, resulting in size reduction of the urethral lumen 517 to facilitate coaptation of urethral mucosa 533 during sphincteric action of the urethral muscle 532. Multiple locations of spiraled filaments 126 can be implanted in urethral muscle 532 to further narrowing the urethral lumen 517, as shown in FIG. 53. For bulking of urethra 516, no filament 126 should be extended into the lumen 517 to avoid infiltration of bacteria into the smooth urethral muscle 532. When closure of urethral lumen 517 with bulking of the filament 126 seems adequate through the cystoscope, the filament 126 between the proximal end 501 of needle handle 130 and bobbin 152 in FIG. 26 is cut, and spiraling of the filament 126 continues with withdrawal, re-advancement and rotation of the needle 101 to completely spiral the remaining filament 126 in needle 101 into urethral muscle 532. The amount of implanted filament 126 is selectable, controllable, limitable or regulateable by the physician. The filament 126 can be a nylon, polypropylene or biodegradable mono-filament suture with some stiffness or shape memory. Coiling or spiraling of the shape memory filament 126 expands within tissue to provide elastic bulking or expansion to enhance the backboard support and sphincteric action of the urethra 516. FIG. 54 shows narrowing of the bladder neck 519 by spirals of filament 126 cushioning, bulking or supporting tissue between the vagina 520 and urethral lumen 517 to relieve stress urinary incontinence and regain sphincteric control.

Gel-like bulking agent has been injected into fecal sphincteric muscle to treat fecal incontinence, but feces can be substantially firm and large to flatten and nullify bulking of the gel-like agent. On the other hand, the elastic and shape-memory spirals of filament 126 are inter-connected to prevent flattening, migration or dislocation, to maintain fecal sphincteric bulking and control, similar to urethral bulking in FIGS. 49-54.

The filament 126 can be a suture 126. The suture 126 spiraling device can also be used to spiral and pack suture 126 under skin to fill indentations from acne scar or cosmetic defect. The spirals of suture 126 at the distal end can also be used as a suture anchor deep within tissue. The proximal end of the suture 126 can be threaded with a tissue repairing needle for tissue fastening through micro-invasive procedure, such as face lift and other suture repair.

The filament 126 or strands 104 of the filament 126 can expand or swell during hydration in body fluid. The swelled filament 126 adds size or mass within tissue to enhance bulking or efficacy of the spirals of filament 126. The filament 126 can also be coated with a hydrophilic or swelling agent, such as polyethylene glycol, collagen, hyaluronic acid or other, for expansion.

The dilator 220 in FIG. 49 can be substituted with the cannula 230 connecting to a luer lock 531 at the proximal end for injection of echogenic liquid. After needle 460 puncturing into urethral muscle 532, the cannula 230 is advanced by sliding over the needle 460 into urethral muscle 532. The needle 460 is withdrawn. Echogenic gel or liquid can be injected through the cannula 230 to confirm distal location of the cannula 230 in urethral muscle 532. Since the cannula 230 has no tissue puncturing capability, injection of echogenic gel for location confirmation may not be necessary. The filament needle 101 is inserted into the cannula 230 for spiraling filament 126.

Figure 55:
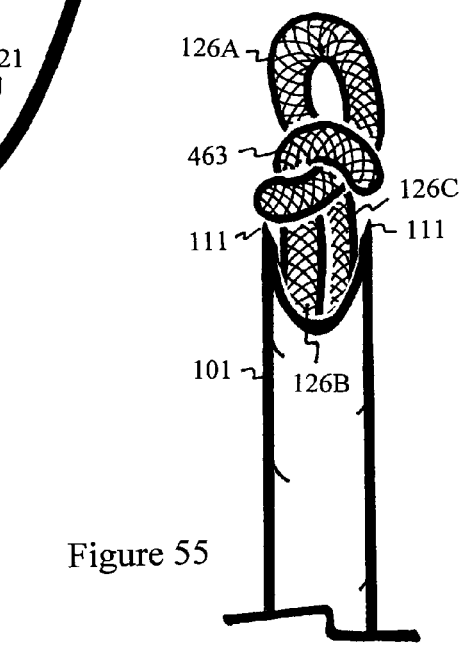
FIG. 55 shows a knot 463 to prevent retraction of the distal end of the filament 126A in the needle 101, and to facilitate filament 126 snagging by the snagging points 231 of cannula 230.
Figure 56:
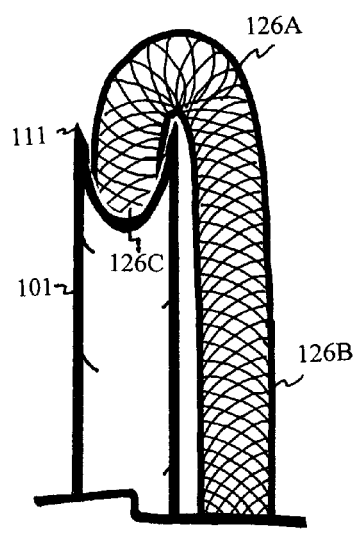
FIG. 56 shows the filament 126C in the needle 101, filament 126B outside the needle 101; and the filament 126A is the distal portion between filament 126C and filament 126B.
Figure 57:
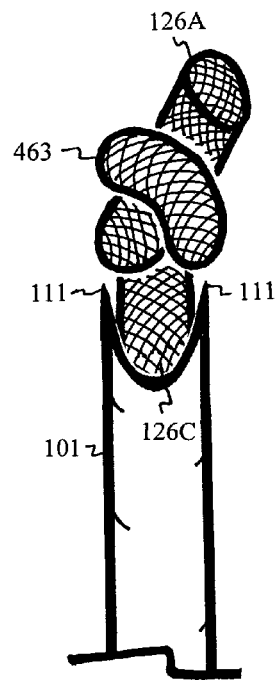
FIG. 57 shows a linear or single stranded filament 126 tied with a knot 463 extending from the needle 101.
Figure 58:
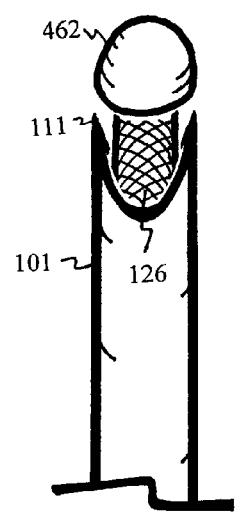
FIG. 58 shows an anchor, knob or toggle 462 on a linear filament 126 extending from the needle 101 to facilitate filament 126 snagging by the cannula 230.

A knot 463 can be tied at the distal portion 126A of the filament 126 to prevent retrieval of the filament 126 into the lumen 269 of the needle 101, as shown in FIG. 55. The knot 463 also facilitates catching or hooking by the snagging point 231 of the cannula 230, further improved from FIG. 25. The U-strand of the filament 126 can be divided into distal portion 126A and proximal portions 126B and 126C. A proximal portion 126B of the filament 126 can drape outside, while another proximal portion 126C of the filament 126 can be inserted in the needle 101 as shown in FIG. 56. A single stranded filament 126 can be inserted into the needle 101, as shown in FIG. 57. The single stranded filament 126 can also be snagged by the snagging points 231 of the cannula 230 and rotated into spiraled filament 126. A knot 463 is tied at the distal portion 126A to prevent retrieval of the single stranded filament 126 into the lumen 269 of the needle 101, as shown in FIG. 57. An anchor 462 can be attached at the distal end of the filament 126, as shown in FIG. 58. The anchor 462 can be made with a biodegradable material or tablet of a pH buffer, nutrients or medication. The anchor 462 can also be a toggle 462, a protrusion 462 or latch 462.

Figure 59:
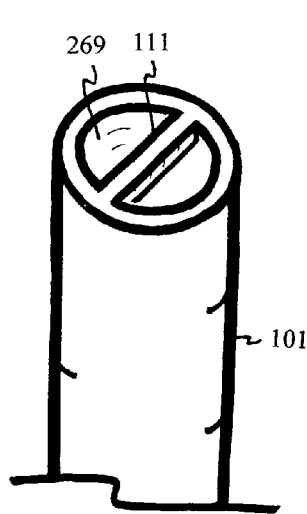
FIG. 59 shows a cross bar 111 as a filament gripper 111.
Figure 60:
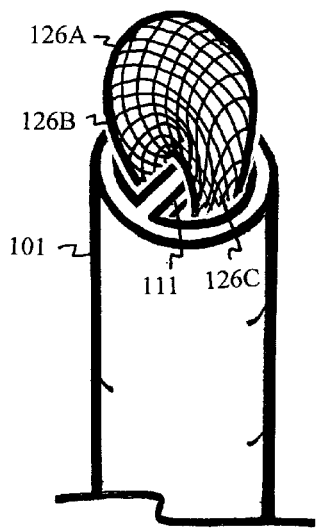
FIG. 60 shows the filament 126 looping over the cross bar 111 for filament 126 spiraling.
Figure 61:
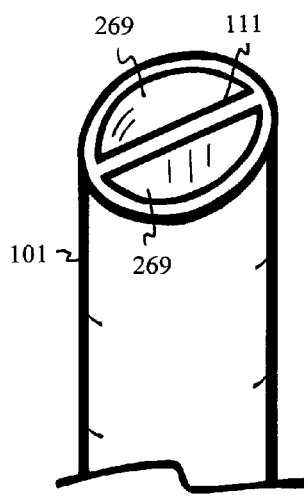
FIG. 61 shows a cross plane 111 as a filament gripper 111, dividing the cylindrical lumen 269 into semi-cylinders 269 for housing the filament strand 126C and filament strand 126B.
Figure 62:
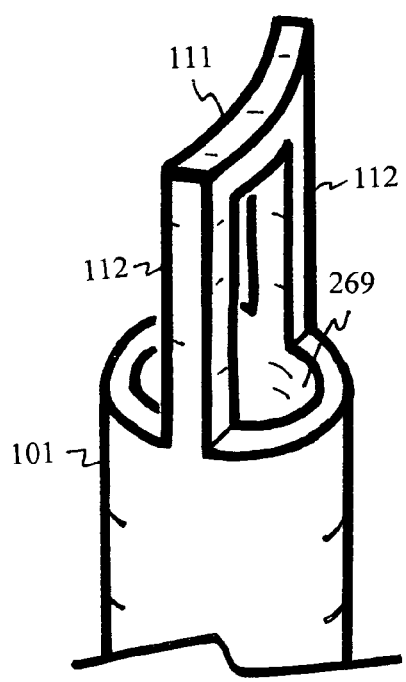
FIG. 62 shows an extended cross bar 111 as a filament gripper 111 connecting to extension bars 112. The extended cross bar 111 can also be an extended cross plane within the lumen 269.
Figure 63:
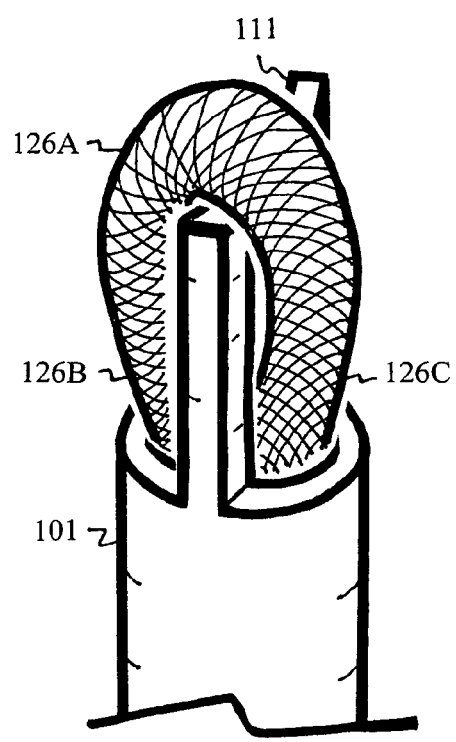
FIG. 63 shows the filament 126 looping over the extended cross bar 111 or extended cross plane 111 for spiraling and pushing of the filament 126.
Figure 64:
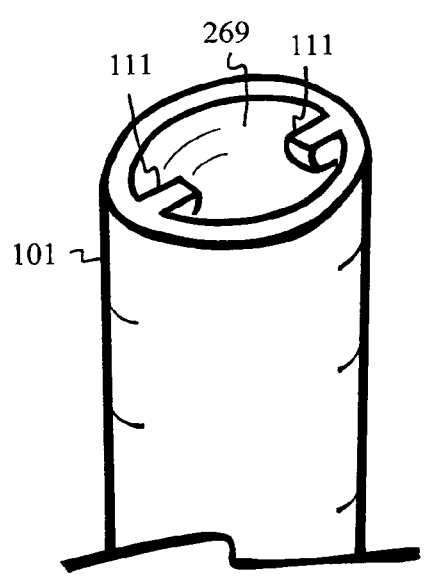
FIG. 64 shows cross stubs 111 as a filament gripper 111 for spiraling and pushing of the filament 126.
Figure 65:
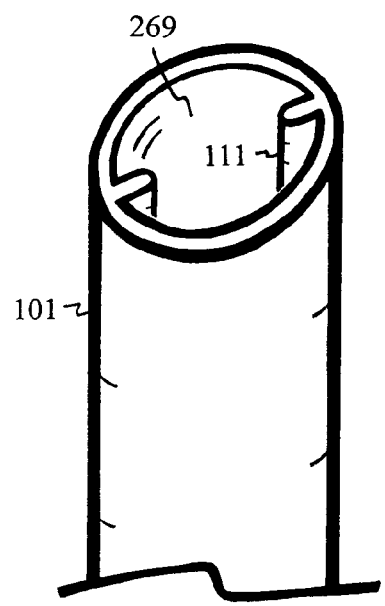
FIG. 65 shows longitudinal cross stubs 111 along the lumen 269 of the needle 101 for spiraling and pushing of the filament 126.

The filament gripper 111 can be a cross bar 111 as shown in FIG. 59. The filament 126 loops over the cross bar 111, as shown in FIG. 60, for insertion into the cannula 230. The cross bar 111 can be a longitudinal plane, dividing the cylindrical lumen 269 of the needle 101 into two semi-cylindrical lumens 269, as shown in FIG. 61. The cross bar 111 or cross plane 111 can tightly pack the spiraled filament 126 into tissue. The cross bar 111 can be extended by two extension bars 112 as shown in FIG. 62. The filament 126 loops over the extended cross bar 111, as shown in FIG. 63. The extended cross bar 111 can also be extended into a cross plane 111, dividing into two semi-cylindrical lumens 269. Filament grippers 111 can be cross stubs 111 as shown in FIG. 64. The cross stubs 111 can also be two longitudinal stubs length-wise through the lumen 269, as shown in FIG. 65.

Loading filament 126 from the bobbin 152 into proximal lumen 269 of the needle 101 is driven by holding the distal end 126A of the filament 126 and withdrawing the needle 101, as shown in FIGS. 25, 26 and 32. A filament advancer 526 can be manually used or motorized to advance the filament 126 without needle 101 withdrawal. The filament advancer 526 contains a stem 527 attaching resiliently collapsible barbs 528 pointing distally, as shown in FIG. 66. The resiliently collapsible barbs 528 have a closed and open positions. In the closed position, the distal ends of the resiliently collapsible barbs 528 approximate the stem 527, solid lines of FIG. 67. In the open position, the distal ends of the resiliently collapsible barbs 528 depart or move outward from the stem 527, in dashed lines of FIG. 67. In operation within tissue, distal end of the filament advancer 526 and the resiliently collapsible barbs 528 are concealed and operated within the lumen 269 of the needle 101. The needle lumen 269 can be non-circular shape. Cross-section of the lumen 269 can contain two connecting circular lumens 269, one for housing the filament advancer 526 and the other for housing the filament 126, similar configuration as FIG. 70A. The opening between the two connecting circular lumens 269 allows the collapsible barbs 528 to extend and engage with the filament 126. During distal movement of the filament advancer 526, the collapsible barbs 528 are in the open positions to grip, puncture, insert, hold, grab, attach, engage, hook or latch on the filament 126, moving the filament 126 distally. During proximal movement of the filament advancer 526, the resiliently collapsible barbs 528 release the engagement with the filament 126 and retract, retrieve or collapse into the closed positions to approximating the stem 527. The collapsible barbs 528 are elastic or flexible to grip and release the filament 126 during cyclical distal-proximal movement of the stem 527 or filament advancer 526. The collapsible barbs 528 are spaced out along the stem 527. The axial or vertical view of the filament advancer 526 in FIG. 68 shows orientations of the resiliently collapsible barb 528 approximately 120 degrees apart. FIG. 69 shows the collapsible barbs 528 approximately 90 degrees apart. The filament 126 can also be advanced by a manually driven or motorized rotational auger 526 as filament advancer 526 within the lumen 269 of the needle 101, as shown in FIG. 70. The auger 526 contains a stem 527 and screw-like or helical thread 528 to engage, convey or propel the filament 126 out the needle 101. In operation within tissue, distal end of the filament advancer 526 and the screw-like thread 528 are concealed and operated within the lumen 269 of the needle 101. The needle lumen 269 can also be non-circular shaped. Cross-section of the lumen 269 can contain two connecting circular lumens 269, one for housing the rotational auger 526 and the other for housing the filament 126, as shown in FIG. 70A. The opening between the two connecting circular lumens 269 allows the screw-like thread 528 to extend and engage with the filament 126. The motorized speed of the resiliently collapsible barbs 528 and screw-like thread 528 can be controlled by a foot pedal. During high torque, a torque sensor initiates reduction or stopping of the motor. The motorized filament advancer 526 saves surgical time and allows physician to concentrate on needle 101 rotation and pushing to pack filament 126 for repairing tissue. The resiliently collapsible barbs 528 and the screw-like thread 528 can be called the filament engager 528 of the filament advancer 526.

Figure 71:
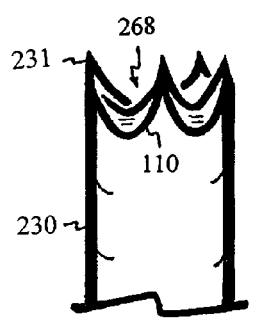
FIG. 71 shows a cannula 230 with multiple snagging points 231.
Figure 72:
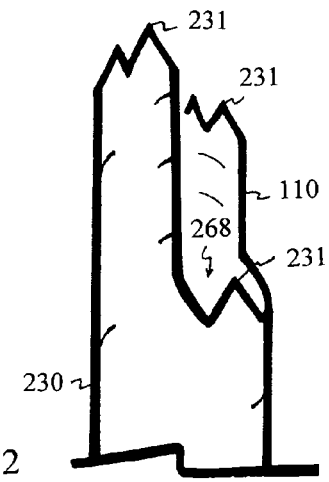
FIG. 72 shows a cannula 230 with a window 110 open to a snagging point 231.
Figure 73:
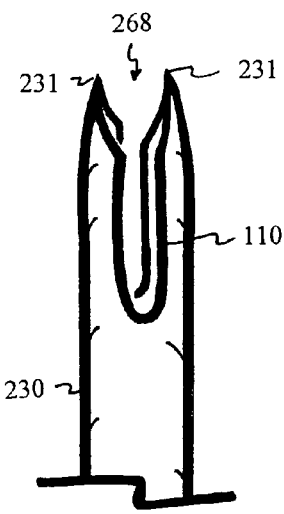
FIG. 73 shows snagging points 231 of a cannula 230 with inward bending or curvatures.
Figure 74:
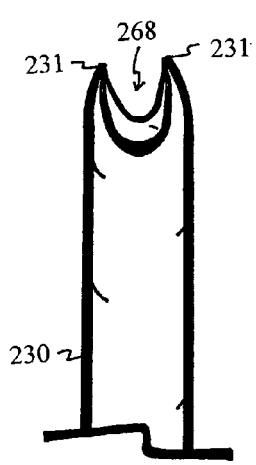
FIG. 74 shows curvatures of snagging points 231 of another cannula 230.
Figure 75:
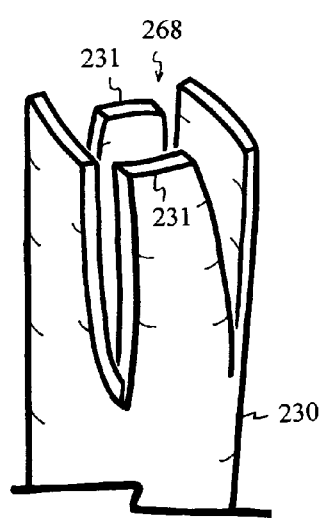
FIG. 75 shows inward bending or curving walls or gates 231 as snagging points 231 at the distal end of the cannula 230.
Figure 76:
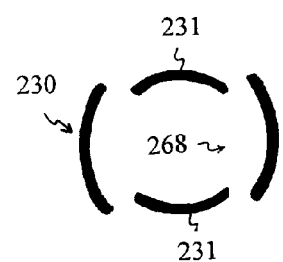
FIG. 76 shows a cross-sectional view of the inward bending gates 231 of the cannula 230.

FIG. 71 shows a cannula 230 with multiple snagging points 231 to facilitate holding on the filament 126. FIG. 72 shows a large window 110 for filament 126 to protrude during needle re-advancement to prevent jamming. The window 110 is open to a snagging point 231. FIG. 73 shows elastically curved or inward bending of snagging points 231 of the cannula 230 to facilitate trapping or hooking of the extended filament 126 in FIGS. 22-25, 27-28, 32, 46, 50, 55-58, 60, 63 from the needle 101. The cannula 230 with elastically curved snagging points 231 can be made with nickel-titanium alloy or nitinol. During advancement of the filament needle 101, the elastically curved snagging points 231 resiliently open or straighten to allow passing of the needle 101 and the extended filament 126. The elastically curved snagging points 231 provide inward grip to trap, catch or hook the extended filament 126, similar to the result of FIGS. 25 and 32. Other elastically curved snagging points 231 of the cannula 230 are shown in FIG. 74. The snagging points 231 can be elastically curved walls or gates 231 at the distal end of the cannula 230 in FIG. 75 to hook or trap the extended filament 126 from the needle 101. FIG. 76 shows a cross-sectional view of the inward bending or elastically curved gates 231, restricting the distal lumen 268 of the cannula 230. The elastic snagging point 231 can be called a spring biased arm 231.

Figure 77:
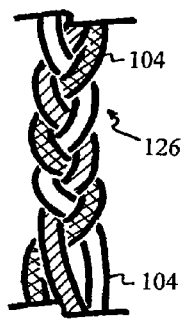
FIG. 77 shows braided strands 104 forming the filament 126.
Figure 78:
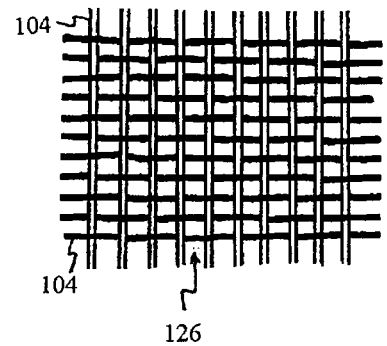
FIG. 78 shows woven strands 104 forming the filament 126.
Figure 79:
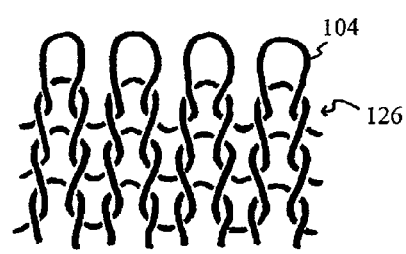
FIG. 79 shows knitted strands 104 forming the filament 126.

Flexible filament 126 can be made or formed by fabric making techniques, such as braiding or twisting strands 104 as shown in FIG. 77. For twisting, minimum number of strands 104 is two. For braiding, minimum number of strands 104 is three, as shown in FIG. 77. Braiding or intertwining three or more strands 104 provides excellent flexibility, strength and porosity of the filament 126. The snagging point 231 of cannula 230 and gripper 111 of needle 101 can catch, snag or engage the filament 126 well. The flexible filament 126 can also be woven, as shown in FIG. 78. Weaving is interlacing the strands 104 over and under each other, generally oriented at 90 degree angles. Half of the strands 104 from weaving can be oriented length-wise along the linear filament 126, to expedite capillarity or fluid flow from the muscle 193 or diffusion zones 106A, 106B into the degenerated disc 100. The flexible filament 126 can be knitted, as shown in FIG. 79. Knitting is a construction made by interlocking loops of one or more strands 104. A knitted filament 126 may have the greatest elastic expansion and compression capability, delivering the most fluid transport or exchange between disc 100 and body circulation during compression and relaxation of the disc 100. In addition, the knitted filament 126 in coils, spirals or reels may have the highest porosity to enhance fluid absorbency, creating a reservoir of nutrients/oxygen/pH buffer 131 for dispersing into various parts of the avascular disc 100, as shown in FIGS. 39-40. Furthermore, the coiled or spiraled filament 126 with knitted strands 104 provides an elastic cushion within the disc 100 to reduce loading and pain in the facet joints 129. The knitted filament 126 may be an excellent matrix or scaffolding for cell 277 attachment and proliferation. The knitted filament 126 may also provide highly expandable spirals for bulking sphincters to regain urinary or fecal control. The filament 126 can be made with non-woven strands 104. The term non-woven is used in fabric industry to include all other techniques, such as carded/needle-punched, spunbonded, melt blown or other. Non-woven filament 126 can provide large surface area as scaffolding for cell 277 growth and proliferation. Combinations of fabric making techniques for the filament 126 can also be used with the needle 101 and cannula 230.

Material and/or orientation of the filaments 126 can affect (1) flow rate, (2) tensile strength, (3) annular sealing, (4) porosity, (5) fluid absorbency, (6) snagging ability, (7) elasticity, (8) selectivity of solute transport, (9) scaffold attachment of cells, (10) flexibility, (11) durability, (12) sterilization technique, (13) fibrotic formation, (14) biocompatibility, and/or (15) bulking. A filament 126 is cut at a slanted angle, showing a cross-section of a filament 126; the strands 104 are slanted or diagonally oriented to the length-wise filament

Figure 80:
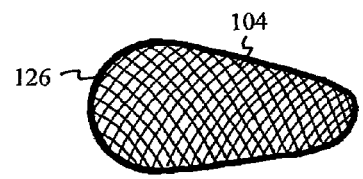
FIG. 80 depicts a slanted cut of the filament 126, showing the slanted orientations of strands 104 relative to length-wise of the filament 126.
Figure 81:
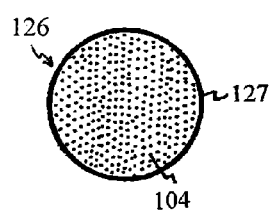
FIG. 81 shows a cross-section of the filament 126 made with parallel strands 104 wrapped, encircled, covered or enveloped by a sheath or cover 127.
Figure 82:
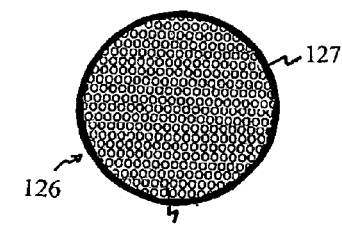
FIG. 82 shows a cross-section of the filament 126 made with parallel tubes 104 wrapped, encircled, covered or enveloped by a sheath or cover 127.

126, as shown in FIG. 80. FIG. 81 shows cross-sections of strands 104 parallel to the filament 126, covered by a wrapper, sheath or cover 127. The parallel-oriented strands 104 and wrapper 127 can be manufactured by extrusion. The strands 104 can also be micro tubes, as shown in FIG. 82, parallel to the filament 126. A wrapper 127 is used to cover, retain, enclose or house the micro strands 104 to form a filament 126. An individual micro tubular strand 104 is capable of having capillary action, drawing nutrients/oxygen/pH buffer 131 through the filament 126 into the disc 100.

The strands 104 are preferred to be made with biocompatible and hydrophilic material, absorbing, retaining or drawing fluid with nutrients/oxygen/pH buffer solutes 131 from a tissue with low osmolarity to mid layer of the desiccated disc 100 with high osmolarity. The filament 126 can be a suture, approved for human implant. Instead of fastening tissue, the suture is used as the filament 126, transporting fluid from low to high osmolarity to alleviate back pain.

Figure 83:
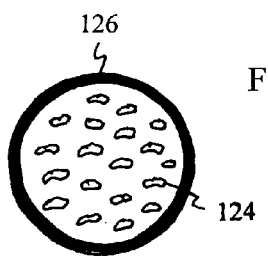
FIG. 83 shows a cross-section of the filament 126 made with sponge or foam with pores 124.
Figure 84:
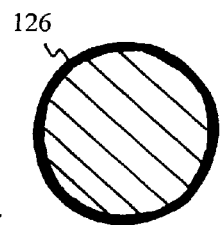
FIG. 84 shows a cross-section of a solid filament 126, similar to a mono-filament suture.

The filament 126 can be made with a hydrophilic sponge or foam with pores 124, as shown in FIG. 83, to transport and retain fluid in the disc 100. The pores 124 can be open, connecting to other pores 124. The pores 124 can also be closed, not connecting to other pores 124 to retain fluid and cells 277. The filament 126 can be solid, pore-less or dense, as shown in cross section in FIG. 84. The solid filament 126 is similar to a mono-filament suture 126. The mono-filament 126 is relatively stiff or contains a shape-memory to resist a spiral or coiled configuration. The spiraled mono-filament 126 elastically expands within tissue, which is suitable for elastic bulking of sphincters to treat urinary or fecal incontinence.

Disc cells 277 isolated from advanced degenerated human discs 100 are still capable of producing collagen and glycosaminoglycans in tissue culture with abundant supply of nutrients in proper pH. (Gruber H. E., Leslie K., Ingram J., Hoelscher G., Norton H. J., Hanley E. N. Jr.: Colony formation and matrix production by human anulus cells: modulation in three-dimensional culture, Spine, Jul. 1, 29(13), E267-274, 2004. Johnstone B, Bayliss M T: The large proteoglycans of the human intervertebral disc, Changes in their biosynthesis and structure with age, topography, and pathology, Spine, March 15; 20(6):674-84, 1995.) Furthermore, stem cells have recently been found in degenerated discs. (Risbud M V, Gattapalli A, Tsai T T, Lee J Y, Danielson K G, Vaccaro A G, Albert T J, Garzit Z, Garzit D, Shapiro I M: Evidence for skeletal progenitor cells in the degenerate human intervertebral disc, Spine, November 1; 32(23), 2537-2544, 2007.) Nutrient 131 deficiency and acidic pH may hinder disc 100 repair in-vivo.

The filament 126 or shunt 126 can be scaffolds and spigots for supplying nutrients/oxygen/pH buffering solute 131 for cell 277 attachment, as shown in FIG. 42. With a continual or renewable supply of nutrients/oxygen/pH buffer solutes 131, disc cells 277 resume making biosynthetic products 160, such as the water-retaining glycosaminoglycans and collagen, the major components of the nucleus 128 and annulus 378. In sheep study, newly formed glycosaminoglycans on nylon strands 104 of the shunt 126 after 3 months can be seen using Safranin histological staining.

The rate of sulfate incorporation for biosynthesizing glycosaminoglycans is pH sensitive. The maximum rate of sulfate incorporation is with pH 7.2-6.9. The rate of sulfate incorporation drops about 32-40% in acidic pH within the disc [Ohshima H, Urban J P: The effect of lactate and pH on proteoglycan and protein synthesis rates in the intervertebral disc. Spine, September: 17(9), 1079-82, 1992]. Hence, pH normalization with pH buffer solute 131 through the shunt 126 will likely increase production of the water-retaining glycosaminoglycans and swelling pressure of the shunted disc 100.

With a continual supply of nutrients 131, newly formed biosynthetic products 160 increase osmolarity within the shunted disc 100 and enhance inward fluid flow, as shown in FIGS. 40 and 42. The increased fluid flow comes through (1) the external shunt 126, (2) blood capillaries 107 through the endplates 105, and/or (3) annulus 378. The fluid is also retained by the newly formed water-retaining glycosaminoglycans 160. As a result, the swelling pressure of the shunted disc 100 increases. Segmental or spinal instability is reduced. Muscle tension and ache from guarding the spinal instability decrease. Load and pain of the facet joints 129 decrease. Lactic acid 162 is further neutralized by inflow of nutrients/oxygen/pH buffering solute 131 to reduce or alleviate acid burn. Disc 100 height is elevated, raised or increased as depicted by arrows in FIGS. 40-41. Implantation of the shunt 126 enables the degenerated disc 100 to be repaired.

Furthermore, adenosine triphosphate, ATP, is the high-energy compound essential for driving or energizing biochemical reactions, including the biosynthesis of the water retaining glycosaminoglycans for sustaining compressive loads on the disc 100. Under anaerobic conditions, metabolism of each glucose molecule produces only two ATP and two lactic acids 162, which irritate adjacent nerves 118. When oxygen 131 permeates through the internal and/or external shunt 126, thirty-six ATP can be produced from each glucose molecule through glycolysis, citric acid cycle and electron transport chain under aerobic conditions to energize disc regeneration and alleviate back pain.

Figure 43:
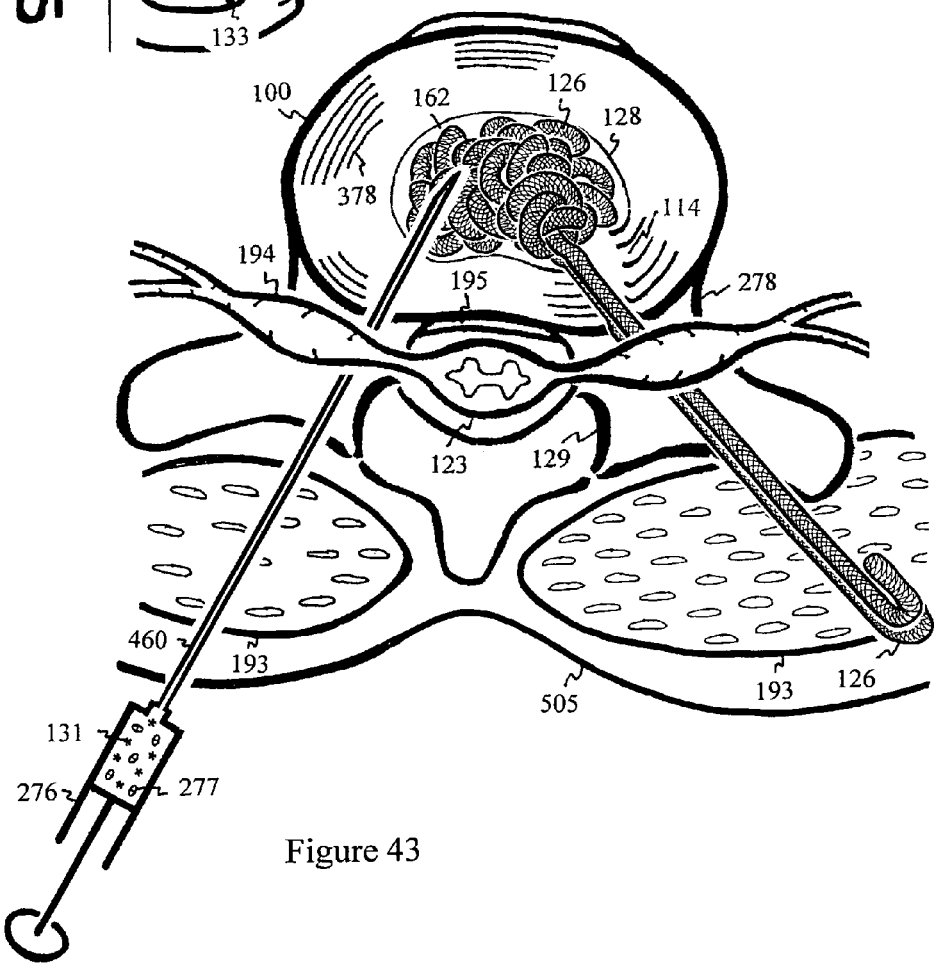
FIG. 43 shows intradiscal injection of nutrients, oxygen and pH buffer 131 and/or cells 277 to facilitate back pain relief and/or disc 100 regeneration.

High concentration of nutrients 131 can also be injected into the internal and/or external shunted disc 100 to instantly create high osmolarity, as shown in FIG. 43. High osmolarity promotes fluid inflow into the shunted disc 100. However, glucose or sugars injection can produce additional lactic acid 162, causing more pain. Sulfate and amino acids can be injected in high concentration to boost osmolarity and production of glycosaminoglycans and collagen, as the biosynthetic product 160 in FIG. 42. Magnesium sulfate, potassium sulfate, or sodium sulfate can be the injectable with high water solubility and is essential for biosynthesis of glycosaminoglycans in the nucleus pulposus 128. Proline and glycine can also be injectables with high water solubility and are essential nutrients 131 for biosynthesis of collagen in the annulus 378.

Analgesics, anti-depressant, steroid, NSAID, antibiotics, anti-inflammatory drugs, alkaline agent or other drugs can also be injected into the shunted disc 100 to instantaneously reduce pain.

Autograft disc cells 277 from a healthy disc 100 of the patient can be transplanted into the degenerated and shunted disc 100 to promote disc regeneration and production of biosynthetic product 160, as shown in FIG. 43.

The avascular disc 100 is well sealed and immuno-isolated. Even small ions, such as sulfate, and small molecules, such as proline, are greatly limited from diffusing into the nucleus pulposus 128. The well sealed disc 100 may be able to encapsulate donor cells 277 from a disc 100 of another person, cadaver or even animal without triggering an immune response, and probably not needing anti-rejection drug. For disc 100 regeneration, the donor cells 277 can also be stem cells 277, notochord 277 or chondrocytes 277. The filament 126 or shunt 126 is permeable to nutrients/oxygen/pH buffering solute 131 but impermeable to cells and/or cytokines responsible for triggering an immune reaction. The cells of the immune system include giant cells, macrophages, mononuclear phagocyts, T-cells, B-cells, lymphocytes, Null cells, K cells, NK cells and/or mask cells. The cytckines may also include immunoglobulins, IgM, IgD, IgG, IgE, other antibodies, interleukins, lymphokines, monokines or interferons.

The molecular weights of nutrients 131 and lactic acid 162 are much smaller than the immuno-responsive cells and cytokines. The transport selectivity can be regulated or limited by the size of the pores or channels within the semi-permeable shunt 126. The upper molecular weight cut-off of the shunt 126 can be 100,000 or lower to allow the passage of nutrients and waste but exclude the immuno-responsive cells and cytokines. The semi-permeable shunt 126 may also contain ionic or affinity surfaces to attract nutrients 131 and waste, including lactic acid 162. The surfaces of the semi-permeable shunt 126 can be made, coated or modified to repel, exclude or reject immuno-responsive components.

In recent years, cell transplants from cadavers or live donors have been successful in providing therapeutic benefits. For example, islet cells from a donor pancreas are injected into a type I diabetic patient's portal vein, leading into the liver. The islets begin to function as they normally do in the pancreas by producing insulin to regulate blood sugar. However, to keep the donor cells alive, the diabetic patient requires a lifetime supply of anti-rejection medication, such as cyclosporin A. In addition to the cost of anti-rejection medication, the side effects of these immuno-suppressive drugs may include cancer. The benefit of cell transplant may not out weigh the potential side effects.

The shunted intervertebral disc 100 can be used as a semi-permeable capsule to encapsulate the injected therapeutic donor cells 277 or agent, as shown in FIG. 43, to evade the immune response; hence no life-long immuno-suppressive drug would be required. A variety of donor cells 277 or agent can be harvested and/or cultured from the pituitary gland (anterior, intermediate lobe or posterior), hypothalamus, adrenal gland, adrenal medulla, fat cells, thyroid, parathyroid, pancreas, testes, ovary, pineal gland, adrenal cortex, liver, renal cortex, kidney, thalamus, parathyroid gland, ovary, corpus luteum, placenta, small intestine, skin cells, stem cells, gene therapy, tissue engineering, cell culture, other gland or tissue. The donor cells 277 are immunoisolated within the shunted discs 100, the largest avascular organs in the body, maintained by nutrients/oxygen/pH buffer 131 and waste transport through the shunt 126 or fissure 121. The donor cells 277 can be from human, animal or cell culture. When disc pressure is low during sleep or supine position, nutrients/oxygen/pH buffering solutes 131 are supplied through the shunt 126 to the donor cells 277. During waking hours while the pressure within the disc 100 is high, biosynthesized products 160 by these donor cells 277 are expelled through the shunt 126 into the muscle 193 or through fissures 121 into bodily circulation and target sites.

The biosynthesized product 160 made by the donor cells 277 can be adrenaline, adrenocorticotropic hormone, aldosterone, androgens, angiotensinogen (angiotensin I and II), antidiuretic hormone, atrial-natriuretic peptide, calcitonin, calciferol, cholecalciferol, calcitriol, cholecystokinin, corticotropin-releasing hormone, cortisol, dehydroepiandrosterone, dopamine, endorphin, enkephalin, ergocalciferol, erythropoietin, follicle stimulating hormone, γ-aminobutyrate, gastrin, ghrelin, glucagon, glucocorticoids, gonadotropin-releasing hormone, growth hormone-releasing hormone, human chorionic gonadotrophin, human growth hormone, insulin, insulin-like growth factor, leptin, lipotropin, luteinizing hormone, melanocyte-stimulating hormone, melatonin, mineralocorticoids, neuropeptide Y, neurotransmitter, noradrenaline, oestrogens, oxytocin, parathyroid hormone, peptide, pregnenolone, progesterone, prolactin, pro-opiomelanocortin, PYY-336, renin, secretin, somatostatin, testosterone, thrombopoietin, thyroid-stimulating hormone, thyrotropin-releasing hormone, thyroxine, triiodothyronine, trophic hormone, serotonin, vasopressin, or other therapeutic products. These biosynthetic products 160 have low molecular weights and are able to be transported through the shunt 126 and/or fissures 121, while the donor cells 277 are trapped within the disc 100.

The biosynthesized products 160 (hormones, peptides, neurotransmitter, enzymes, catalysis or substrates) generated within the shunted disc 100 may be able to regulate bodily functions including blood pressure, energy, neuro-activity, metabolism, and activation and suppression of gland activities. Some hormones and enzymes govern, influence or control eating habits and utilization of fat or carbohydrates. These hormones or enzymes may provide weight loss or gain benefits. Producing neurotransmitters, such as dopamine, adrenaline, noradrenaline, serotonin or γ-aminobutyrate, from the donor cells 277 within the shunted disc 100 can treat depression, Parkinson's disease, learning disability, memory loss, attention deficit, behavioral problems, mental or neuro-related diseases.

Release of the biosynthesized products 160 by the donor cells 277 within the shunted disc 100 is synchronized with body activity. During activities of daily living, the pressure within the shunted disc 100 is usually high to expel the biosynthesized products 160 by the donor cells 277 into circulation to meet the demands of the body. In the supine position, pressure within the shunted disc 100 is low; fluid inflow 161 through the shunt 126 is favorable, bringing nutrients/oxygen/pH buffer 131 into the disc 100 to nourish the cells 277. As an example, islets of Langerhans from a donor's pancreas can be implanted or injected into the shunted disc 100. In supine position during sleeping, glucose enters into the shunted disc 100 to induce production of insulin from the implanted islets of Langerhans. During waking hours when disc pressure is high, insulin is expelled through the shunts 126 or fissure 121 into circulation to regulate concentration of glucose in the body. At night, the insulin released from the shunted disc 100 is minimal to prevent hypoglycemia. In essence, biosynthesized products 160 by the donor cells 277 are released concurrent with physical activity to meet the demands of the body.

Donor cells 277 can also be seeded on the shunt 126 or injected days, weeks, months or even years after implanting the disc shunts 126, to ensure favorable biological conditions, including pH, electrolytic balance and nutrients and oxygen 131, for cell 277 survival and proliferation in the shunted disc 100.

In the United States, average age of patients undergoing back surgery is about 40-45 years old. The disc shunt 126 is preferred to be made with permanent material to provide long-lasting pain relief. A wide range of non-degradable materials can be used to fabricate the shunt 126. Polymers, such as nylon, polytetrafluoroethylene, polypropylene, polyethylene, polyamide, polyester, polyurethane, silicon, polyether-ether-ketone, acetal resin, polysulfone, polycarbonate, silk, cotton, or linen are possible candidates. Fiberglass can also be a part of the shunt strands 104, to provide capillarity for transporting nutrients 131 and waste.

Especially for investigative purposes, biodegradable shunts 126 may provide evidence within weeks or months. Since the disc shunt 126 degrades within months, any unforeseen adverse outcome would be dissipated. If the investigative-degradable shunt 126 shows promise, permanent shunt 126 can then be implanted to provide continuous benefits.

The biodegradable shunt 126 can be made with polylactate, polyglycolic, poly-lactide-co-glycolide, polycaprolactone, trimethylene carbonate, silk, catgut, collagen, poly-p-dioxanone or combinations of these materials. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate or polyphosphazene can also be used.

The filament needle 101 and cannula 230 can be made with stainless steel, nickel-titanium alloy or other metal or alloy. The needle 101 and cannula 230 can be coated with lubricant, tissue sealant, analgesic, antibiotic, radiopaque, magnetic and/or echogenic agents.

The disc shunt 126 can be used as a drug delivery device, delivering oral, intravenous or injectable drugs into the avascular or nearly impenetrable disc 100 to treat infection, inflammation, pain, tumor or other disease. Drugs can be injected into the muscle 193 to be drawn into the shunted disc 100. Discitis is a painful infection or inflammatory lesion in the intervertebral disc 100 of adults and children (Wenger D R, Bobechko W P, Gilday D L: The spectrum of intervertebral disc-space infection in children, J. Bone Joint Surg. Am., 60:100-108, 1978. Shibayama M, Nagahara M, Kawase G, Fujiwara K, Kawaguchi Y, Mizutani J: New Needle Biopsy Technique for Lumbar Pyogenic Spondylodiscitis, Spine, 1 November, Vol. 35—Issue 23, E1347-E1349, 2010). Due to the avascular nature of the disc 100, oral or intravenous drugs cannot easily reach the bacteria or inflammation within the disc 100. Therefore, discitis is generally difficult to treat. However, the disc shunt 126 can be used as a drug-delivery device. The disc shunt 126 draws the systemic drugs from muscles 193 into the sealed, avascular disc 100. In addition, antibiotics, anti-inflammatory drugs, anesthetics or other drugs can be injected into the muscle 193 near the disc shunt 126 to increase drug concentration within the disc 100 to treat discitis or pain. Injection near the shunt 126 is called perishunt injection.

*Staphylococcus aureus* is the most common bacteria found in discitis. The shunt 126 can be loaded or coated with an antibiotic, such as nafcillin, cefazolin, dicloxacilin, clindamycin, bactrim, penicillin, mupirocin (bactroban), vancomycin, linezolid, rifampin, sulfamethoxazole-trimethoprim or other, to treat *staphylococcus aureus* infection. *Corynebacterium* is also found in discitis. The shunt 126 can be loaded or coated with an antibiotic, such as erythromycin, vancomycin, eifampin, penicillin or tetracycline, to treat *corynebacterium* infection. Other antibiotics, such as cefdinir, metronidazole, timidazole, cephamandole, latamoxef, cefoperazone, cefinenoxime, furazolidone or other, can also be used to coat the shunt 126.

Inflammation in the disc 100 can cause excruciating pain. MRI can show inflammation at the endplates 105, and distinguish inflammatory classification as Modic I, II or III. The disc shunt 126 can be coated or loaded with nonsteroidal anti-inflammatory drugs/analgesics (NSAID), such as aspirin, diflunisal, salsalate, ibuprofen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, licofelone or other NSAID, to treat inflammation in the disc 100 for pain relief.

The disc shunt 126 can also be coated or loaded with steroidal anti-inflammatory drugs/analgesics, such as betamethasone, budesonide, cortisone, dexamethasone, hydrocortisone, methylprednisolone, prednisolone, prednisone, triamcinolone or other steroid, to treat inflammation in the disc 100 for pain relief.

The shunt 126 can be loaded or coated with anesthetics, such as procaine, amethocaine, cocaine, lidocaine, prilocalne, bupivacaine, levobupivacaine, ropivacaine, mepivacaine, dibucaine, methohexital, thiopental, diazepam, lorazepam, midazolam, etomidate, ketamine, propofol, alfentanil, fentanyl, remifentanil, sufentanil, buprenorphine, butorphanol, diamorphine, hydromorphone, levophanol, meperidine, methadone, morphine, nalbuphine, oxycodone, oxymorphone, pentazocine or other anesthetic, to provide instant pain relief.

The shunt 126 can be loaded or coated with a muscle relaxant, such as succinylcholine, decamethonium, mivacurium, rapacuronium, atracurium, cisatracurium, rocuronium, vecuronium, alcuronium, doxacurium, gallamine, metocurine, pancuronium, pipecuronium, tubocurarine or other relaxant, to relieve muscle tension and ache.

The shunt 126 can be loaded or coated with buffering agents, such as sodium carbonate, sodium bicarbonate, potassium carbonate, potassium bicarbonate, magnesium carbonate, calcium carbonate, barium carbonate, potassium phosphate, sodium phosphate or other buffering agent, to neutralize lactic acid 162 and spontaneously alleviate pain caused by acid irritation or burn.

The shunt 126 can be loaded or coated with alkaline agents, such as magnesium oxide, magnesium hydroxide, sodium hydroxide, potassium hydroxide, barium hydroxide, cesium hydroxide, strontium hydroxide, calcium hydroxide, lithium hydroxide, rubidium hydroxide, neutral amines or other alkaline agent, to neutralize lactic acid 162 and spontaneously alleviate pain caused by acid irritation.

The shunt 126 can be loaded or coated with initial supplies of nutrients 131, such as sulfate, glucose, glucuronic acid, galactose, galactosamine, glucosamine, hydroxylysine, hydroxylproline, serine, threonine, chondroitin sulfate, keratan sulfate, hyaluronate, magnesium trisilicate, magnesium mesotrisilicate, magnesium oxide, magnosil, orthosilicic acid, magnesium trisilicate pentahydrate, sodium metasilicate, silanolates, silanol group, sialic acid, silicic acid, boron, boric acid, other mineral, other amino acid or nutrients 131, to enhance or initiate production of sulfated glycosaminoglycans and collagen within the degenerative disc 100.

Oral intake of antidepressants has shown temporary pain reduction or pain tolerance in back pain patients. Anti-depressants can be coated on the shunt 126 to treat chronic back pain. The anti-depressant coating may include tricyclic antidepressant, serotonin-reuptake inhibitor, norepinephrine reuptake inhibitor, serotonin-norepinephrine reuptake inhibitor, noradrenergic/serotonergic antidepressants, norepinephrine-dopamine reuptake inhibitor, serotonin reuptake enhancers, norepinephrine-dopamine disinhibitors or monoamine oxidase inhibitor. The antidepressant can be amitriptyline, amitriptylinoxide, butriptyline, clomipramine, demexiptiline, desipramine, dibenzepin, dimetacrine, dosulepin/ dothiepin, doxepin, duloxetine, imipramine, imipraminoxide, lofepramine, melitracen, metapramine, nitroxazepine, nortriptyline, noxiptiline, pipofezine, propizepine, protriptyline, quinupramine, amineptine, iprindole, opipramol, tianeptine, trimipramine, or other antidepressant.

Fibrous formation over the shunt 126 may affect the exchange of nutrients 131 and waste between the disc 100 and bodily circulation or muscle 193. Immuno inhibitor can be coated or incorporated into the shunt 126 to minimize fibrous formation or tissue response. Examples of immuno inhibitors include but are not limited to: actinomycin-D, aminopterin, azathioprine, chlorambucil, corticosteroids, crosslinked polyethylene glycol, cyclophosphamide, cyclosporin A, 6-mercaptopurine, methylprednisolone, methotrexate, niridazole, oxisuran, paclitaxel, polyethylene glycol, prednisolone, prednisone, procarbazine, prostaglandin, prostaglandin $E_1$, sirolimus, steroids or other immune suppressant drugs.

The shunt 126 can be loaded or coated with a calcium channel blocker for inhibiting activation of neuro-receptor to alleviate pain. The calcium channel blocker can be dihydropyridines, phenylalkylamines, benzothiazepines, magnesium ion, Amlodipine, Felodipine, Isradipine, Lacidipine, Lercanidipine, Nicardipine, Nifedipine, Nimodipine, Nisoldipine, Verapamil, Diltiazem or other calcium channel blocker.

Healthy intervertebral discs 100 are avascular. To ensure avascular conditions, the shunt 126 can be incorporated, coated or partially coated with an anti-angiogenic compound. Examples of anti-angiogenic compounds include, but are not limited to, Marimastat from British Biotech [a synthetic inhibitor of matrix metalloproteinases (MMPs)], Bay 12-9566 from Bayer (a synthetic inhibitor of tumor growth), AG3340 from Agouron (a synthetic MMP inhibitor), CGS 27023A from Novartis (a synthetic MMP inhibitor), COL-3 from Collagenex (a synthetic MMP inhibitor, Tetracycline® derivative), Neovastat from Aeterna, Sainte-Foy (a naturally occurring MMP inhibitor), BMS-275291 from Bristol-Myers Squib (a synthetic MMP inhibitor), TNP-470 from TAP Pharmaceuticals, (a synthetic analogue of fumagillin; inhibits endothelial cell growth), Thalidomide from Celgene (targets VEGF, bFGF), Squalamine from Magainin Pharmaceuticals (Extract from dogfish shark liver; inhibits sodium-hydrogen exchanger, NHE3), Combretastatin A-4 (CA4P) from Oxigene, (induction of apoptosis in proliferating endothelial cells), Endostatin collagen XVIII fragment from EntreMed (an inhibition of endothelial cells), Anti-VEGF Antibody from Genentech, [Monoclonal antibody to vascular endothelial growth factor (VEGF)], SU5416 from Sugen (blocks VEGF receptor signaling), SU6668 from Sugen (blocks VEGF, FGF, and EGF receptor signaling), PTK787/ZK 22584 from Novartis (blocks VEGF receptor signaling), Interferon-alpha (inhibition of bFGF and VEGF production), Interferon-alpha (inhibition of bFGF and VEGF production), EMD121974 from Merck, KcgaA (small molecule blocker of integrin present on endothelial cell surface), CAI from NCl (inhibitor of calcium influx), Interleukin-12 from Genetics Institute (Up-regulation of interferon gamma and IP-10), IM862 from Cytran, Avastin, Celebrex, Erbitux, Herceptin, Iressa, Taxol, Velcade, TNP-470, CM101, Carboxyamidotriazole, Anti-neoplastic urinary protein, Isotretionin, Interferon-alpha, Tamoxifen, Tecogalan combrestatin, Squalamine, Cyclophosphamide, Angiostatin, Platelet factor-4, Anginex, Eponemycin, Epoxomicin, Epoxy-β-aminoketone, Antiangiogenic antithrombin III, Canstatin, Cartilage-derived inhibitor, CD59 complement fragment, Fibronectin fragment, Gro-beta, Heparinases, heparin hexasaccharide fragment, Human chorinonic gonadotropin, Interferon (alpha, beta or gamma), Interferon inducible protein (IP-10), Interleukin-12 (IL-12), Kringle 5 (plasminogen fragment), Tissue inhibitors of metalloproteinases, 2-Methoxyestradiol (Panzem), Placental ribonuclease inhibitor, Plasminogen activator inhibitor, Prolactin 16 kD fragment, Retinoids, Tetrahydrocortisol-S, Thrombospondin-1, Transforming growth factor beta, Vasculostatin, and Vasostatin (calreticulin fragment).

The shunt 126 can be loaded or coated with lactic acid inhibitor or lactate dehydrogenase inhibitor. The lactic acid inhibitor or lactate dehydrogenase inhibitor includes fluoropyruvic acid, fluoropyruvate, levulinic acid, levulinate, oxamic acid, N-substituted oxamic acids, oxamate, oxalic acid, oxalate, beta-bromopropionate, beta-chloropropionate, malonate, sodium formaldehyde bisufite, chloroacetic acid, alpha-chloropropionate, alpha-bromopropionate, beta-iodopropionate, acrylate, acetoin, malic acid, glycolate, diglycolate, acetamide, acetaldehyde, acetylmercaptoacetic acid, alpha ketobutyrate, thioglycolic acid, nicotinic acid, alpha-ketoglutarate, butanedione, hydroxypyruvic, chloropyruvic, bromopyruvic, 2,3-dihydroxy-6-methyl-4-(1-methylethyl)-1-naphthoic acid, diethyl pyrocarbonate, hexyl N,N-diethyloxamate, 3-acetylpyridine adenine dinucleotide, 7-p-Trifluoromethylbenzyl-8-deoxyhemigossylic acid, dihydroxynaphthoic acids, N-substituted oxamic acids, gossypol, gossylic iminolactone, derivatives of gossypol, dihydroxynaphthoic acid, 2,3-dihydroxy-6-methyl-4-(1-methylethyl)-1-naphthoic acid, blue dye, reactive blue dye #2 (Cibacron Blue 3G-A) urea, methylurea and hydantoic acid, glyoxylate, hydroxybutyrate, 4-hydroxyquinoline-2-3 carboxylic acids, sodium bisulfite, dieldrin, L-(+) beta monofluorolactic acid, fluoro-lactic acid, tartronic acid, mesotartarate, sesquiterpene 8-deoxyhemigossylic acid (2,3-dihydroxy-6-methyl-4-(1-methylethyl)-1-naphthoic acid), or analogues of these chemicals.

In summary, the disc shunt 126 alleviates back pain by (1) drawing nutrients/oxygen/pH buffer 131 into the disc 100, (2) neutralizing lactic acid 162 to alleviate acid burn, (3) converting anaerobic to aerobic conditions to reduce lactic acid 162 production, (4) increasing sulfate incorporation in neutral pH for biosynthesis of glycosaminoglycans. (5) increasing ATP production from aerobic metabolism of sugars to drive biosynthetic reactions in disc 100, (6) bulking up the disc 100 to take load off painful facet joints 129, (7) fortifying the disc 100 to reduce spinal instability and muscle tension, (8) rebuilding disc matrix to increase osmolarity, fluid intake and absorption, (9) re-establishing the swelling pressure to sustain disc 100 compression, (10) regenerating the disc 100 for long term pain relief, and/or (11) delivering systemic drugs in disc 100 to treat discitis.

Unlike many surgical interventions of the spine, benefits of the disc shunt 126 include (1) spinal motion preservation, (2) no tissue removal, (3) reversible by extraction, (4) micro-invasive, (5) out-patient procedure, (6) approved implant material, (7) 15-minutes per disc, (8) long-lasting and no-harm-done, (9) no incision, (10) compatible with drugs, conservative treatment or surgical intervention, if needed, and (11) drug coated shunt if needed to expedite pain relief.

The present invention of the shunt 126 or filament 126 is spirally formed distal to a needle 101 and cannula 230, packing into a disc 100, reaching one or both diffusion zones 106A, 106B between 0 and 3 mm from the endplates 105, to draw nutrients/oxygen/pH buffer 131 diffused from capillaries 107 at the endplate 105 into the mid layer of the disc 100. Nutrients and cells 277 can be intradiscally injected for disc regeneration and/or production of biosynthetic product 160.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments. A pH electrode may be exposed near the tip of the needle 101 to detect the acidity within the disc 100.

It should be clear to one skilled in the art that the current embodiments, materials, constructions, methods, tissues or incision sites are not the only uses for which the invention may be used. Different materials, constructions, methods or designs for various sections 126A, 126B and 126C can be substituted and used. The disc shunt 126 can be called a filament, strand, thread, line, conduit, wick, sponge or absorbent. Spiraled shunt 126 can be called a coiled shunt or coiled filament 126. The snagging point 231 can be called the snagger 231. The filament gripper 111 can be called the gripper 111. Nothing in the preceding description should be taken to limit the scope of the present invention. The full scope of the invention is to be determined by the appended claims.

What is claimed is:

1. A deployment device for implanting a selectable amount of filament within a tissue, the deployment device comprising:
    a cannula capable of being guided such that a distal tip thereof may be located within an implant location of the tissue,
    a filament comprises a proximal portion and a distal portion,
    a filament needle comprises a proximal end, a distal end, and a lumen,
        wherein said distal portion of said filament is sized and configured to fit in said lumen,
    said distal end of said filament needle and said distal portion of said filament locatable within said cannula,
    said distal portion of said filament is capable of being advanced generally parallel and distal to said filament needle, thereby delivering said distal portion of said filament sized and configured into the implant location,
    and said filament needle is capable of being rotated, thereby spiraling said distal portion into a twisted distal portion of said filament.

2. The deployment device of claim 1, wherein said filament needle is capable of being retracted proximally and advanced distally more than once, thereby delivering multiple distal portions of said filament sized and configured into the implant location.

3. The deployment device of claim 1, further comprising an advancer, wherein said advancer is sized and configured to engage at least a portion of said filament.

4. The deployment device of claim 3, wherein said advancer is a helically threaded auger.

5. The deployment device of claim 3, wherein said advancer is an elongated body comprising one or more barbs located along a length thereof.

6. The deployment device of claim 1, wherein said distal tip of said cannula comprises at least one filament snagger, and wherein said at least one filament snagger is sized and configured to engage at least a portion of said filament.

7. The deployment device of claim 6, wherein said at least one filament snagger takes a form of a pointed tip.

8. The deployment device of claim 6, wherein said at least one filament snagger takes a form of a spring biased or elastically curved arm.

9. The deployment device of claim 1, wherein said distal end of said filament needle comprises at least one filament gripper, and wherein said at least one filament gripper is sized and configured to engage at least a portion of said filament.

10. The deployment device of claim 9, wherein said at least one filament gripper takes a form of a distally pointing tip.

11. The deployment device of claim 9, wherein said at least one filament gripper takes a form of a cross bar in said lumen of said filament needle.

12. The deployment device of claim 9, wherein said at least one filament gripper takes a form of a cross plane longitudinally dividing said lumen of said filament needle.

13. The deployment device of claim 9, wherein said at least one filament gripper takes a form of a cross stub in said lumen of said filament needle.

14. The deployment device of claim 9, wherein said at least one filament gripper takes a form of a cross stub longitudinal extending into said lumen of said filament needle.

15. The deployment device of claim 1, wherein said cannula further comprises a proximal section, and wherein said proximal section comprises a funnel.

16. The deployment device of claim 1, wherein said cannula further comprises a proximal section, and wherein said proximal section comprises a latch engaging said filament needle.

17. The deployment device of claim 1, wherein said proximal end of said filament needle comprises a bobbin, and wherein said proximal portion of said filament is spooled over said bobbin.

18. A deployment device for implanting a selectable amount of filament within a tissue, the deployment device comprising:
    a needle capable of reaching and puncturing into an implant location,
    a guide wire comprises a distal length insertable into said needle,
    a dilator comprises a longitudinal opening sized and configured to fit over said guide wire,
    a cannula comprises a longitudinal channel sized and configured to fit over said dilator, wherein said cannula further comprises a distal tip,
    a filament comprises a proximal portion and a distal portion,
    a filament needle comprises a proximal end, a distal end, and a lumen,
        wherein said distal portion of said filament is sized and configured to fit in said lumen,
    said distal end of said filament needle and said distal portion of said filament locatable within said cannula,
    said distal portion of said filament is capable of being advanced generally parallel and distal to said filament needle, thereby delivering said distal portion of said filament sized and configured into the implant location,
    and said filament needle is capable of being rotated, thereby spiraling said distal portion into a twisted distal portion of said filament.

19. The deployment device of claim 18, further comprising an advancer, wherein said advancer is sized and configured to engage at least a portion of said filament.

20. The deployment device of claim 19, wherein said advancer is a helically threaded auger.

21. The deployment device of claim 19, wherein said advancer is an elongated body comprising one or more barbs located along a length thereof.

22. The deployment device of claim 18, wherein said distal tip of said cannula further comprises at least one filament snagger, and wherein said at least one filament snagger is size and configured to engage at least a portion of said filament.

23. The deployment device of claim 22, wherein said at least one filament snagger takes a form of a pointed tip.

24. The deployment device of claim 22, wherein said at least one filament snagger takes a form of a spring biased or elastically curved arm.

25. The deployment device of claim 18, wherein said distal end of said filament needle comprises at least one filament gripper, and wherein said at least one filament gripper is sized and configured to engage at least a portion of said filament.

26. The deployment device of claim 25, wherein said at least one filament gripper takes a form of a distally pointing tip.

27. The deployment device of claim 25, wherein said at least one filament gripper takes a form of a cross bar in said lumen of said filament needle.

28. The deployment device of claim 25, wherein said at least one filament gripper takes a form of a cross plane longitudinally dividing said lumen of said filament needle.

29. The deployment device of claim 25, wherein said at least one filament gripper takes a form of a cross stub in said lumen of said filament needle.

30. The deployment device of claim 25, wherein said at least one filament gripper takes a form of a cross stub longitudinal extending into said lumen of said filament needle.

31. The deployment device of claim 18, wherein said filament needle is capable of being retracted proximally and advanced distally more than once, thereby delivering multiple distal portions of said filament sized and configured into the implant location.

32. The deployment device of claim 18, wherein said cannula further comprises a proximal section, and wherein said proximal section comprises a funnel.

33. The deployment device of claim 18, wherein said cannula further comprises a proximal section, and wherein said proximal section comprises a latch engaging said filament needle.

34. The deployment device of claim 18, wherein said proximal end of said filament needle comprises a bobbin, and wherein said proximal portion of said filament is spooled over said bobbin.

* * * * *